US008083716B2

(12) United States Patent
Kavazov et al.

(10) Patent No.: US 8,083,716 B2
(45) Date of Patent: Dec. 27, 2011

(54) SYSTEMS AND METHODS ALLOWING FOR RESERVOIR AIR BUBBLE MANAGEMENT

(75) Inventors: Julian D. Kavazov, Arcadia, CA (US); Sheldon B. Moberg, Thousand Oaks, CA (US); Ian B. Hanson, Northridge, CA (US); Colin A. Chong, Burbank, CA (US); Eric M. Lorenzen, Granada Hills, CA (US); Rafael Bikovsky, Oak Park, CA (US); Truong Gia Luan, Winnetka, CA (US); Mike Lee, Glendale, CA (US); Christopher G. Griffin, Sylmar, CA (US); Thomas Miller, Valencia, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 329 days.

(21) Appl. No.: 11/964,649

(22) Filed: Dec. 26, 2007

(65) Prior Publication Data
US 2008/0269681 A1 Oct. 30, 2008

Related U.S. Application Data

(60) Provisional application No. 60/927,032, filed on Apr. 30, 2007.

(51) Int. Cl.
*A61M 1/00* (2006.01)
(52) U.S. Cl. ........ 604/123; 604/122; 604/124; 604/125; 604/222; 604/151
(58) Field of Classification Search .......... 604/187–240, 604/122–127, 151–155
See application file for complete search history.

(56) References Cited

U.S. PATENT DOCUMENTS

| 1,948,982 | A | * | 2/1934 | Cutter ........................... 604/222 |
| 2,064,815 | A | | 12/1936 | Armstrong |
| 2,570,625 | A | | 10/1951 | Zimmerman et al. |
| 2,644,450 | A | | 7/1953 | Krewson |
| 2,973,758 | A | | 3/1961 | Murrish |
| 3,342,180 | A | * | 9/1967 | Sandhage et al. ............... 604/89 |
| 3,623,474 | A | | 11/1971 | Heilman et al. |

(Continued)

FOREIGN PATENT DOCUMENTS
DE 10 2004 055 870 A1 5/2006
(Continued)

OTHER PUBLICATIONS

PCT search report dated Feb. 3, 2009 from PCT Application No. PCT/US2008/082185.

(Continued)

*Primary Examiner* — Jackie Ho
*Assistant Examiner* — Leah Stohr
(74) *Attorney, Agent, or Firm* — Foley & Lardner LLP

(57) ABSTRACT

Various embodiments of the present invention are directed to limiting a presence of air bubbles in a fluidic medium expelled from a reservoir. In various embodiments, a plunger head within a reservoir is shaped so as to limit a presence of air bubbles in a fluidic medium expelled from the reservoir. Also, in various embodiments, a reservoir is shaped so as to limit a presence of air bubbles in a fluidic medium expelled from the reservoir. In some embodiments, both a reservoir and a plunger head within the reservoir are shaped so as to limit a presence of air bubbles in a fluidic medium expelled from the reservoir.

38 Claims, 23 Drawing Sheets

U.S. PATENT DOCUMENTS

| | | | |
|---|---|---|---|
| 3,662,753 A * | 5/1972 | Tassell | 604/89 |
| 3,802,430 A | 4/1974 | Schwebel et al. | |
| 3,963,151 A | 6/1976 | North, Jr. | |
| 4,064,879 A | 12/1977 | Leibinsohn | |
| 4,089,624 A | 5/1978 | Nichols et al. | |
| 4,117,841 A | 10/1978 | Perrotta et al. | |
| 4,215,701 A | 8/1980 | Raitto | |
| 4,219,055 A | 8/1980 | Wright | |
| 4,373,535 A | 2/1983 | Martell | |
| 4,392,850 A | 7/1983 | Elias et al. | |
| 4,434,820 A | 3/1984 | Glass | |
| 4,448,206 A | 5/1984 | Martell | |
| 4,493,704 A * | 1/1985 | Beard et al. | 604/154 |
| 4,568,336 A | 2/1986 | Cooper | |
| 4,572,210 A | 2/1986 | McKinnon | |
| 4,585,435 A | 4/1986 | Vaillancourt | |
| 4,684,365 A | 8/1987 | Reinicke | |
| 4,684,366 A | 8/1987 | Denny et al. | |
| 4,703,763 A | 11/1987 | McAlister et al. | |
| 4,743,249 A | 5/1988 | Loveland | |
| 4,744,955 A | 5/1988 | Shapiro | |
| 4,759,756 A | 7/1988 | Forman et al. | |
| 4,838,857 A | 6/1989 | Strowe et al. | |
| 4,865,592 A | 9/1989 | Rycroft | |
| 4,883,101 A | 11/1989 | Strong | |
| 4,913,703 A | 4/1990 | Pasqualucci et al. | |
| 4,957,637 A | 9/1990 | Cornell | |
| 4,976,696 A | 12/1990 | Sanderson et al. | |
| 4,986,820 A * | 1/1991 | Fischer | 604/218 |
| 4,994,034 A * | 2/1991 | Botich et al. | 604/110 |
| 5,002,527 A | 3/1991 | Reller et al. | |
| 5,049,129 A | 9/1991 | Zdeb et al. | |
| 5,053,001 A | 10/1991 | Reller et al. | |
| 5,062,834 A | 11/1991 | Gross et al. | |
| 5,090,963 A | 2/1992 | Gross et al. | |
| 5,156,591 A | 10/1992 | Gross et al. | |
| 5,176,502 A | 1/1993 | Sanderson et al. | |
| 5,186,805 A | 2/1993 | Gross et al. | |
| 5,190,522 A | 3/1993 | Wojcicki et al. | |
| 5,203,506 A | 4/1993 | Gross et al. | |
| 5,232,449 A | 8/1993 | Stern et al. | |
| 5,242,406 A | 9/1993 | Gross et al. | |
| 5,242,408 A | 9/1993 | Jhuboo et al. | |
| 5,246,147 A | 9/1993 | Gross | |
| 5,254,096 A | 10/1993 | Rondelet et al. | |
| 5,259,732 A | 11/1993 | Stern | |
| 5,261,884 A | 11/1993 | Stern et al. | |
| 5,275,582 A | 1/1994 | Wimmer | |
| 5,284,570 A | 2/1994 | Savage et al. | |
| 5,292,318 A | 3/1994 | Haber et al. | |
| 5,295,966 A | 3/1994 | Stern et al. | |
| 5,295,967 A | 3/1994 | Rondelet et al. | |
| 5,312,364 A | 5/1994 | Jacobs | |
| 5,356,632 A | 10/1994 | Gross et al. | |
| 5,367,891 A | 11/1994 | Furuyama | |
| 5,385,559 A | 1/1995 | Mannix | |
| 5,387,450 A | 2/1995 | Stewart | |
| 5,407,434 A | 4/1995 | Gross | |
| 5,409,236 A | 4/1995 | Therrien | |
| 5,425,706 A | 6/1995 | Gross et al. | |
| 5,496,285 A | 3/1996 | Schumacher et al. | |
| 5,527,288 A | 6/1996 | Gross et al. | |
| 5,533,964 A | 7/1996 | Halperin et al. | |
| 5,697,916 A | 12/1997 | Schraga | |
| 5,704,520 A | 1/1998 | Gross | |
| 5,800,420 A | 9/1998 | Gross et al. | |
| 5,807,375 A | 9/1998 | Gross et al. | |
| 5,820,622 A | 10/1998 | Gross et al. | |
| 5,848,991 A | 12/1998 | Gross et al. | |
| 5,851,549 A | 12/1998 | Svec | |
| 5,858,001 A | 1/1999 | Tsals et al. | |
| 5,865,803 A | 2/1999 | Major | |
| 5,871,125 A | 2/1999 | Gross | |
| 5,933,287 A | 8/1999 | Muller | |
| 5,951,523 A | 9/1999 | Osterlind et al. | |
| 5,954,697 A | 9/1999 | Srisathapat et al. | |
| 5,957,889 A | 9/1999 | Poulsen et al. | |
| 5,984,894 A | 11/1999 | Poulsen et al. | |
| 5,997,501 A | 12/1999 | Gross et al. | |
| 6,003,736 A | 12/1999 | Ljunggren | |
| 6,033,377 A | 3/2000 | Rasmussen et al. | |
| 6,088,608 A | 7/2000 | Schulman et al. | |
| 6,099,504 A | 8/2000 | Gross et al. | |
| 6,119,028 A | 9/2000 | Schulman et al. | |
| 6,126,643 A | 10/2000 | Vaillancouert | |
| 6,186,982 B1 | 2/2001 | Gross et al. | |
| 6,229,584 B1 | 5/2001 | Chuo et al. | |
| 6,242,665 B1 | 6/2001 | Malowaniec | |
| 6,248,093 B1 | 6/2001 | Moberg | |
| 6,261,272 B1 | 7/2001 | Gross et al. | |
| 6,275,717 B1 | 8/2001 | Gross et al. | |
| 6,277,095 B1 | 8/2001 | Kriesel et al. | |
| 6,312,409 B1 | 11/2001 | Gross | |
| 6,314,317 B1 | 11/2001 | Willis | |
| 6,346,095 B1 | 2/2002 | Gross et al. | |
| 6,364,865 B1 | 4/2002 | Lavi et al. | |
| 6,406,455 B1 | 6/2002 | Willis et al. | |
| 6,423,035 B1 | 7/2002 | Das et al. | |
| 6,440,096 B1 | 8/2002 | Lastovich et al. | |
| 6,450,993 B1 | 9/2002 | Lin | |
| 6,461,329 B1 | 10/2002 | Van Antwerp et al. | |
| 6,474,219 B2 | 11/2002 | Klitmose et al. | |
| 6,478,771 B1 | 11/2002 | Lavi et al. | |
| 6,485,461 B1 | 11/2002 | Mason et al. | |
| 6,485,465 B2 | 11/2002 | Moberg et al. | |
| 6,490,483 B2 | 12/2002 | Willis | |
| 6,503,225 B1 * | 1/2003 | Kirsch et al. | 604/126 |
| 6,508,788 B2 | 1/2003 | Preuthun | |
| 6,537,251 B2 | 3/2003 | Klitmose | |
| 6,551,285 B1 | 4/2003 | Bierman | |
| 6,572,600 B1 | 6/2003 | Roe et al. | |
| 6,585,707 B2 | 7/2003 | Cabiri et al. | |
| 6,589,229 B1 | 7/2003 | Connelly et al. | |
| 6,595,956 B1 | 7/2003 | Gross et al. | |
| 6,607,513 B1 | 8/2003 | Down et al. | |
| 6,613,019 B2 | 9/2003 | Munk | |
| 6,616,627 B2 | 9/2003 | Willis et al. | |
| 6,626,874 B1 | 9/2003 | Duchamp | |
| 6,641,565 B1 | 11/2003 | Lavi et al. | |
| 6,641,566 B2 | 11/2003 | Douglas et al. | |
| 6,645,181 B1 | 11/2003 | Lavi et al. | |
| 6,656,147 B1 | 12/2003 | Gertsek et al. | |
| 6,656,158 B2 | 12/2003 | Mahoney et al. | |
| 6,656,159 B2 | 12/2003 | Flaherty | |
| 6,669,669 B2 | 12/2003 | Flaherty et al. | |
| 6,689,100 B2 | 2/2004 | Connelly et al. | |
| 6,692,457 B2 | 2/2004 | Flaherty | |
| 6,699,218 B2 | 3/2004 | Flaherty et al. | |
| 6,702,779 B2 | 3/2004 | Connelly et al. | |
| 6,715,516 B2 | 4/2004 | Ohms et al. | |
| 6,716,195 B2 | 4/2004 | Nolan, Jr. et al. | |
| 6,719,734 B1 | 4/2004 | Harkless | |
| 6,723,068 B2 | 4/2004 | Lavi et al. | |
| 6,723,072 B2 | 4/2004 | Flaherty et al. | |
| 6,740,059 B2 | 5/2004 | Flaherty | |
| 6,740,072 B2 | 5/2004 | Starkweather et al. | |
| 6,749,587 B2 | 6/2004 | Flaherty | |
| 6,767,188 B2 | 7/2004 | Vrane et al. | |
| 6,768,425 B2 | 7/2004 | Flaherty et al. | |
| 6,786,246 B2 | 9/2004 | Ohms et al. | |
| 6,796,965 B2 | 9/2004 | Dumaresq-Lucas et al. | |
| 6,808,506 B2 | 10/2004 | Lastovich et al. | |
| 6,827,702 B2 | 12/2004 | Lebel et al. | |
| 6,830,558 B2 | 12/2004 | Flaherty et al. | |
| 6,830,560 B1 | 12/2004 | Gross et al. | |
| 6,886,724 B2 | 5/2005 | Hung | |
| 6,899,699 B2 | 5/2005 | Enggaard | |
| 6,915,147 B2 | 7/2005 | Lebel et al. | |
| 6,936,006 B2 | 8/2005 | Sabra | |
| 6,939,324 B2 | 9/2005 | Gonnelli et al. | |
| 6,948,918 B2 | 9/2005 | Hansen | |
| 6,952,604 B2 | 10/2005 | DeNuzzio et al. | |
| 6,960,184 B2 | 11/2005 | Willis et al. | |
| 6,960,192 B1 | 11/2005 | Flaherty et al. | |
| 6,997,911 B2 | 2/2006 | Klitmose | |
| 7,008,399 B2 | 3/2006 | Larsen et al. | |
| 7,018,360 B2 | 3/2006 | Flaherty et al. | |

| | | |
|---|---|---|
| 7,027,478 B2 | 4/2006 | Ackley |
| 7,029,455 B2 | 4/2006 | Flaherty |
| 7,083,592 B2 | 8/2006 | Lastovich et al. |
| 7,083,599 B2 | 8/2006 | Alchas et al. |
| 7,115,108 B2 | 10/2006 | Wilkinson et al. |
| 7,128,727 B2 | 10/2006 | Flaherty et al. |
| 7,133,329 B2 | 11/2006 | Skyggebjerg et al. |
| 7,137,964 B2 | 11/2006 | Flaherty |
| 7,144,384 B2 | 12/2006 | Gorman et al. |
| 7,150,409 B2 | 12/2006 | Gonnelli et al. |
| 7,156,838 B2 | 1/2007 | Gabel et al. |
| 7,187,969 B2 | 3/2007 | Willis |
| 7,220,245 B2 | 5/2007 | Kriesel |
| 7,220,889 B2 | 5/2007 | Sigurjonsson et al. |
| 7,323,142 B2 | 1/2008 | Pendo et al. |
| 7,390,294 B2 | 6/2008 | Hassler, Jr. |
| 7,399,484 B2 | 7/2008 | Ellefson et al. |
| 7,686,787 B2 | 3/2010 | Moberg et al. |
| 7,858,112 B2 | 12/2010 | Hatanaka et al. |
| 2001/0041869 A1 | 11/2001 | Causey, III et al. |
| 2002/0040208 A1 | 4/2002 | Flaherty et al. |
| 2002/0072733 A1 | 6/2002 | Flaherty |
| 2002/0123740 A1 | 9/2002 | Flaherty et al. |
| 2002/0126036 A1 | 9/2002 | Flaherty et al. |
| 2002/0169439 A1 | 11/2002 | Flaherty |
| 2003/0055380 A1 | 3/2003 | Flaherty |
| 2003/0073952 A1 | 4/2003 | Flaherty et al. |
| 2003/0097092 A1 | 5/2003 | Flaherty |
| 2003/0104032 A1 | 6/2003 | Sawhney et al. |
| 2003/0125672 A1 | 7/2003 | Adair et al. |
| 2003/0167035 A1 | 9/2003 | Flaherty et al. |
| 2003/0167036 A1 | 9/2003 | Flaherty |
| 2003/0199824 A1 | 10/2003 | Mahoney et al. |
| 2003/0199825 A1 | 10/2003 | Flaherty |
| 2003/0212364 A1 | 11/2003 | Mann et al. |
| 2003/0229310 A1 | 12/2003 | Flaherty et al. |
| 2003/0233069 A1 | 12/2003 | Gillespie et al. |
| 2004/0010207 A1 | 1/2004 | Flaherty et al. |
| 2004/0011866 A1 | 1/2004 | Saad |
| 2004/0015131 A1 | 1/2004 | Flaherty et al. |
| 2004/0064088 A1 | 4/2004 | Gorman et al. |
| 2004/0064096 A1 | 4/2004 | Flaherty et al. |
| 2004/0073095 A1 | 4/2004 | Causey, III et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0116866 A1 | 6/2004 | Gorman et al. |
| 2004/0158207 A1 | 8/2004 | Hunn et al. |
| 2004/0199140 A1 | 10/2004 | Rue et al. |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0236201 A1 | 11/2004 | Lebel et al. |
| 2004/0260233 A1 | 12/2004 | Garibotto et al. |
| 2005/0022274 A1 | 1/2005 | Campbell et al. |
| 2005/0065760 A1 | 3/2005 | Murtfeldt et al. |
| 2005/0101920 A1* | 5/2005 | Keane et al. ................ 604/218 |
| 2005/0119618 A1 | 6/2005 | Gonnelli |
| 2005/0137530 A1 | 6/2005 | Campbell et al. |
| 2006/0184119 A1 | 8/2006 | Remde et al. |
| 2006/0253085 A1 | 11/2006 | Geismar et al. |
| 2006/0264835 A1 | 11/2006 | Nielsen et al. |
| 2007/0062068 A1 | 3/2007 | Li |
| 2007/0066939 A1 | 3/2007 | Krulevich et al. |
| 2007/0073235 A1 | 3/2007 | Estes et al. |
| 2007/0293826 A1 | 12/2007 | Wall et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0051714 A1 | 2/2008 | Moberg et al. |
| 2008/0051716 A1 | 2/2008 | Stutz |
| 2008/0051718 A1 | 2/2008 | Kavazov et al. |
| 2008/0051727 A1 | 2/2008 | Moberg et al. |
| 2008/0051738 A1 | 2/2008 | Griffin |
| 2008/0051765 A1 | 2/2008 | Mounce |
| 2008/0077081 A1 | 3/2008 | Mounce et al. |
| 2008/0097291 A1 | 4/2008 | Hanson et al. |
| 2008/0097321 A1 | 4/2008 | Mounce et al. |
| 2008/0097326 A1 | 4/2008 | Moberg et al. |
| 2008/0097327 A1 | 4/2008 | Bente et al. |
| 2008/0097328 A1 | 4/2008 | Moberg et al. |
| 2008/0097375 A1 | 4/2008 | Bikovsky |
| 2008/0097381 A1 | 4/2008 | Moberg et al. |
| 2008/0269682 A1* | 10/2008 | Kavazov et al. ............. 604/126 |

FOREIGN PATENT DOCUMENTS

| | | |
|---|---|---|
| DE | 20 2007 006 363 U1 | 8/2007 |
| EP | 1 462 134 A1 | 9/2004 |
| EP | 1 527 792 A1 | 5/2005 |
| EP | 1 347 705 | 12/2005 |
| EP | 1 423 079 | 7/2006 |
| EP | 1 135 056 | 8/2006 |
| EP | 1 545 657 | 11/2006 |
| EP | 1 546 556 | 12/2006 |
| EP | 1 341 569 | 1/2007 |
| EP | 1 461 070 | 1/2007 |
| EP | 1 464 351 | 1/2007 |
| EP | 1 309 366 | 2/2007 |
| EP | 0 944 648 | 3/2007 |
| EP | 1 646 412 | 3/2007 |
| EP | 1 095 668 | 4/2007 |
| EP | 1 702 635 | 1/2008 |
| FR | 1.496.026 | 9/1967 |
| GB | 1 452 104 | 10/1976 |
| GB | 2 176 711 A | 1/1987 |
| GB | 2 207 652 A | 2/1989 |
| WO | WO 95/32015 | 11/1995 |
| WO | WO 96/26702 | 9/1996 |
| WO | WO 97/44078 | 11/1997 |
| WO | WO 97/46203 | 12/1997 |
| WO | WO 99/48546 | 9/1999 |
| WO | WO-99/59665 | 11/1999 |
| WO | WO-00/47254 | 8/2000 |
| WO | WO 00/69488 | 11/2000 |
| WO | WO 01/70307 | 9/2001 |
| WO | WO-01/76684 A1 | 10/2001 |
| WO | WO 02/02165 A2 | 1/2002 |
| WO | WO-02/20073 A2 | 3/2002 |
| WO | WO-02/28454 A2 | 4/2002 |
| WO | WO-02/40083 A2 | 5/2002 |
| WO | WO-02/49509 A2 | 6/2002 |
| WO | WO-02/068015 A2 | 9/2002 |
| WO | WO-03/006090 A1 | 1/2003 |
| WO | WO-03/024504 A2 | 3/2003 |
| WO | WO 03/026728 A1 | 4/2003 |
| WO | WO-03/033051 A1 | 4/2003 |
| WO | WO-03/059372 A3 | 7/2003 |
| WO | WO 03/072172 A2 | 9/2003 |
| WO | WO-03/074121 A1 | 9/2003 |
| WO | WO-03/090509 A2 | 11/2003 |
| WO | WO-03/090819 A2 | 11/2003 |
| WO | WO-03/090838 A1 | 11/2003 |
| WO | WO-03/103758 A1 | 12/2003 |
| WO | WO-03/103763 A1 | 12/2003 |
| WO | WO 2004/006981 A2 | 1/2004 |
| WO | WO-2004/006982 A2 | 1/2004 |
| WO | WO 2004/030716 | 4/2004 |
| WO | WO 2004/030717 | 4/2004 |
| WO | WO-2004/047641 A2 | 6/2004 |
| WO | WO-2004/060436 A2 | 7/2004 |
| WO | WO-2004/093648 A2 | 11/2004 |
| WO | WO-2004/098390 A2 | 11/2004 |
| WO | WO-2004/098454 A2 | 11/2004 |
| WO | WO 2004/098683 A1 | 11/2004 |
| WO | WO 2004/110526 A1 | 12/2004 |
| WO | WO 2005/000382 A2 | 1/2005 |
| WO | WO 2005/072795 A2 | 8/2005 |
| WO | WO-2005/094920 A1 | 10/2005 |
| WO | WO 2005/097237 A1 | 10/2005 |
| WO | WO-2006/015922 A1 | 2/2006 |
| WO | WO-2006/018425 A3 | 2/2006 |
| WO | WO-2006/018447 A3 | 2/2006 |
| WO | WO-2006/024671 A1 | 3/2006 |
| WO | WO-2006/024672 A1 | 3/2006 |
| WO | WO-2006/032692 A1 | 3/2006 |
| WO | WO-2006/042811 A3 | 4/2006 |

| | | | |
|---|---|---|---|
| WO | WO 2006/058435 A2 | 6/2006 |
| WO | WO-2006/072416 A2 | 7/2006 |
| WO | WO-2006/075016 A1 | 7/2006 |
| WO | WO-2006/077262 A1 | 7/2006 |
| WO | WO-2006/077263 A1 | 7/2006 |
| WO | WO-2006/084464 A1 | 8/2006 |
| WO | WO-2006/086980 A1 | 8/2006 |
| WO | WO-2006/089547 A1 | 8/2006 |
| WO | WO-2006/089548 A1 | 8/2006 |
| WO | WO-2006/089965 A1 | 8/2006 |
| WO | WO-2006/096746 A1 | 9/2006 |
| WO | WO-2006/097453 A1 | 9/2006 |
| WO | WO-2006/104806 A2 | 10/2006 |
| WO | WO-2006/108775 A2 | 10/2006 |
| WO | WO-2006/108809 A1 | 10/2006 |
| WO | WO-2006/116997 A1 | 11/2006 |
| WO | WO-2006/120253 A2 | 11/2006 |
| WO | WO-2006/125692 A1 | 11/2006 |
| WO | WO-2007/000425 A2 | 1/2007 |
| WO | WO-2007/000426 A2 | 1/2007 |
| WO | WO-2007/000427 A1 | 1/2007 |
| WO | WO-2007/038091 A2 | 4/2007 |
| WO | WO 2007062068 A2 | 5/2007 |
| WO | WO-2007/071255 A1 | 6/2007 |
| WO | WO-2007/076641 A1 | 7/2007 |
| WO | PCT/US2007/76641 | 8/2007 |
| WO | WO-2007/087808 A1 | 8/2007 |
| WO | WO 2007/130809 A2 | 11/2007 |
| WO | WO 2008/024614 A2 | 2/2008 |
| WO | WO 2008/093063 A2 | 8/2008 |
| WO | WO 2008/151241 A2 | 12/2008 |

OTHER PUBLICATIONS

Partial PCT Search Report (Invitation to Pay Additional Fees) dated Feb. 2, 2009 for related PCT application No. PCT/US2008/082186.
Partial PCT Search Report dated Mar. 5, 2009 from related PCT application No. PCT/US2008/082187.
PCT Search Report dated Apr. 28, 2009 from related PCT application No. PCT/US2008/082186.
Office Action dated Jan. 29, 2009 from related U.S. Appl. No. 11/604,172.
Office Action dated Nov. 24, 2008 from related U.S. Appl. No. 11/759,725.
Office Action dated Apr. 13, 2009 from related U.S. Appl. No. 11/604,171.
Office Action dated Apr. 9, 2009 from related U.S. Appl. No. 11/515,225.
PCT Search Report dated May 15, 2008 for PCT application No. PCT/US2007/076679.
PCT Search Report Dated Jun. 5, 2009 from related PCT application No. PCT/US2008/082187.
Office Action dated Apr. 30, 2009 from related U.S. Appl. No. 12/027,963.
Office Action dated Jul. 10, 2009 from related U.S. Appl. No. 12/411,236.
Office Action dated Aug. 4, 2009 from related U.S. Appl. No. 12/411,247.
Final Office Action dated Jun. 17, 2009 from related U.S. Appl. No. 11/604,172.
Notice of Allowance dated Jun. 23, 2009 from related U.S. Appl. No. 11/759,725.
Final Office Action dated Sep. 24, 2009 from related U.S. Appl. No. 12/027,963.
Final Office Action dated Oct. 23, 2009 from related U.S. Appl. No. 12/411,236.
Non-Final Office Action dated Nov. 10, 2009 from related U.S. Appl. No. 12/099,738.
Office Action dated Dec. 22, 2010 from related U.S. Appl. No. 12/111,815.
Office Action dated Dec. 30, 2010 from related U.S. Appl. No. 12/107,580.
Office Action dated Dec. 9, 2010 from related U.S. Appl. No. 12/099,738.
US Office Action dated Oct. 15, 2010 from related U.S. Appl. No. 12/027,963.
International Search Report and Written Opinion for PCT application No. PCT/US2008/082193 dated Jun. 29, 2010.
Office Action dated Jul. 21, 2010 from related U.S. Appl. No. 12/099,738.
Office Action dated Jun. 16, 2010 from related U.S. Appl. No. 12/027,963.
US Office Action dated Aug. 18, 2010 from related patent application number on U.S. Appl. No. 12/107,580.
U.S. Office Action dated Mar. 8, 2011 from related U.S. Appl. No. 12/411,247.
US Notice of Allowance dated Mar. 3, 2011 from related U.S. Appl. No. 12/107,580.
US Office Action dated Feb. 23, 2011 from related U.S. Appl. No. 12/411,236.
International Search Report and Written Opinion for PCT patent application No. PCT/US2007/076474 dated Feb. 29, 2008.
Notice of Allowance dated Jan. 19, 2010 from related U.S. Appl. No. 11/759,725.
Office Action dated Feb. 17, 2010 from related U.S. Appl. No. 11/604,172.
Office Action dated Jan. 14, 2010 from related U.S. Appl. No. 12/411,247.
Office Action dated Mar. 2, 2010 from related U.S. Appl. No. 11/588,832.
Office Action dated Mar. 4, 2010 from related U.S. Appl. No. 12/099,738.
Office Action dated Nov. 19, 2008 from related U.S. Appl. No. 11/515,225.
Office Action dated Nov. 21, 2008 from related U.S. Appl. No. 11/588,832.
Office Action dated Nov. 21, 2008 from related U.S. Appl. No. 11/604,171.
Office Action dated Oct. 19, 2009 from related U.S. Appl. No. 11/515,225.
Office Action dated Oct. 9, 2009 from related U.S. Appl. No. 11/604,171.
Search Report dated Jan. 11, 2010 from related European patent application No. 07841183.2.
US Office Action dated Oct. 1, 2010 U.S. Appl. No. 12/411,247.
US Office Action dated Sep. 28, 2010 from related U.S. Appl. No. 12/411,236.
US Notice of Allowance dated Jul. 27, 2011 from related U.S. Appl. No. 12/411,247.

* cited by examiner

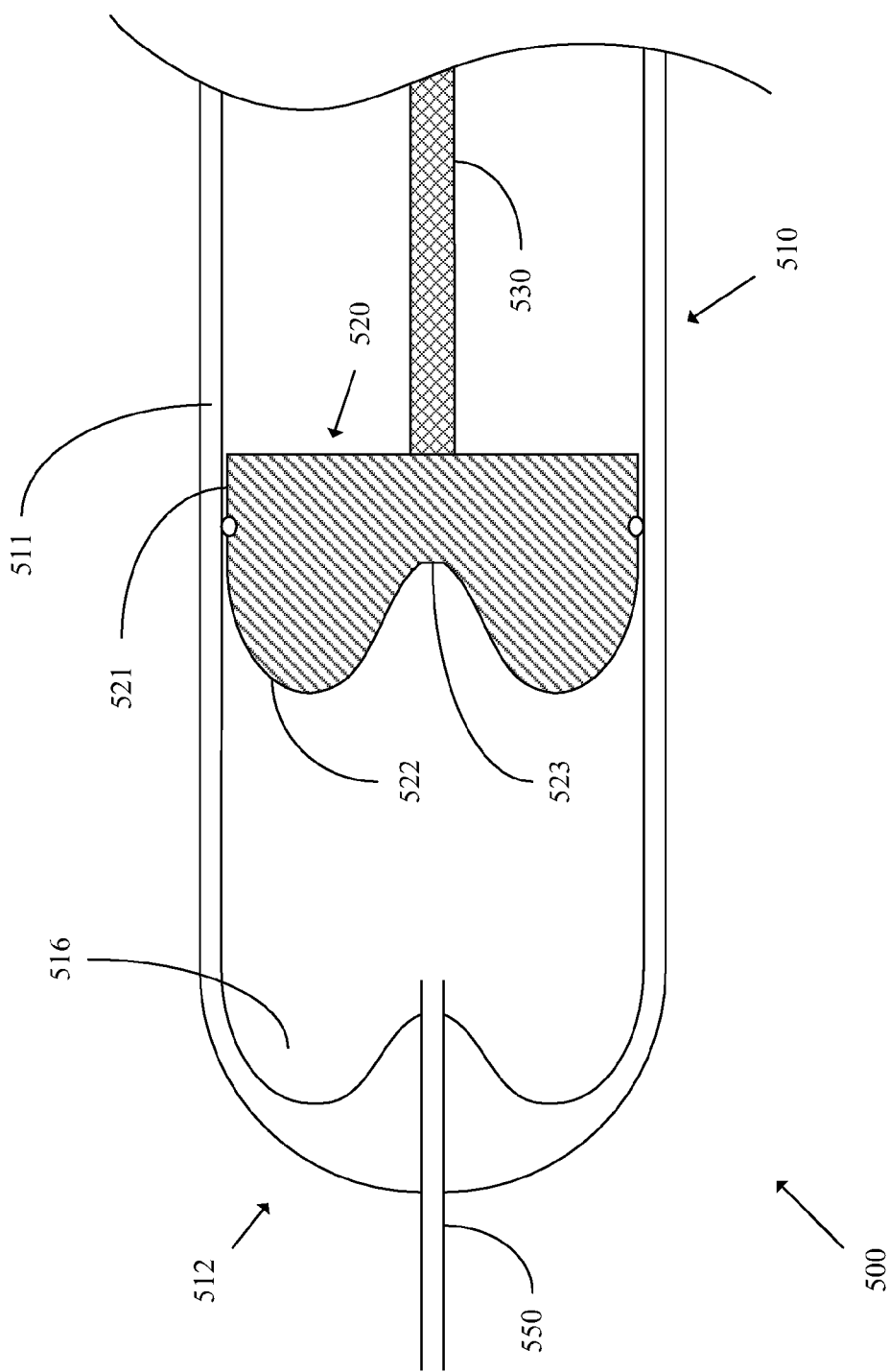

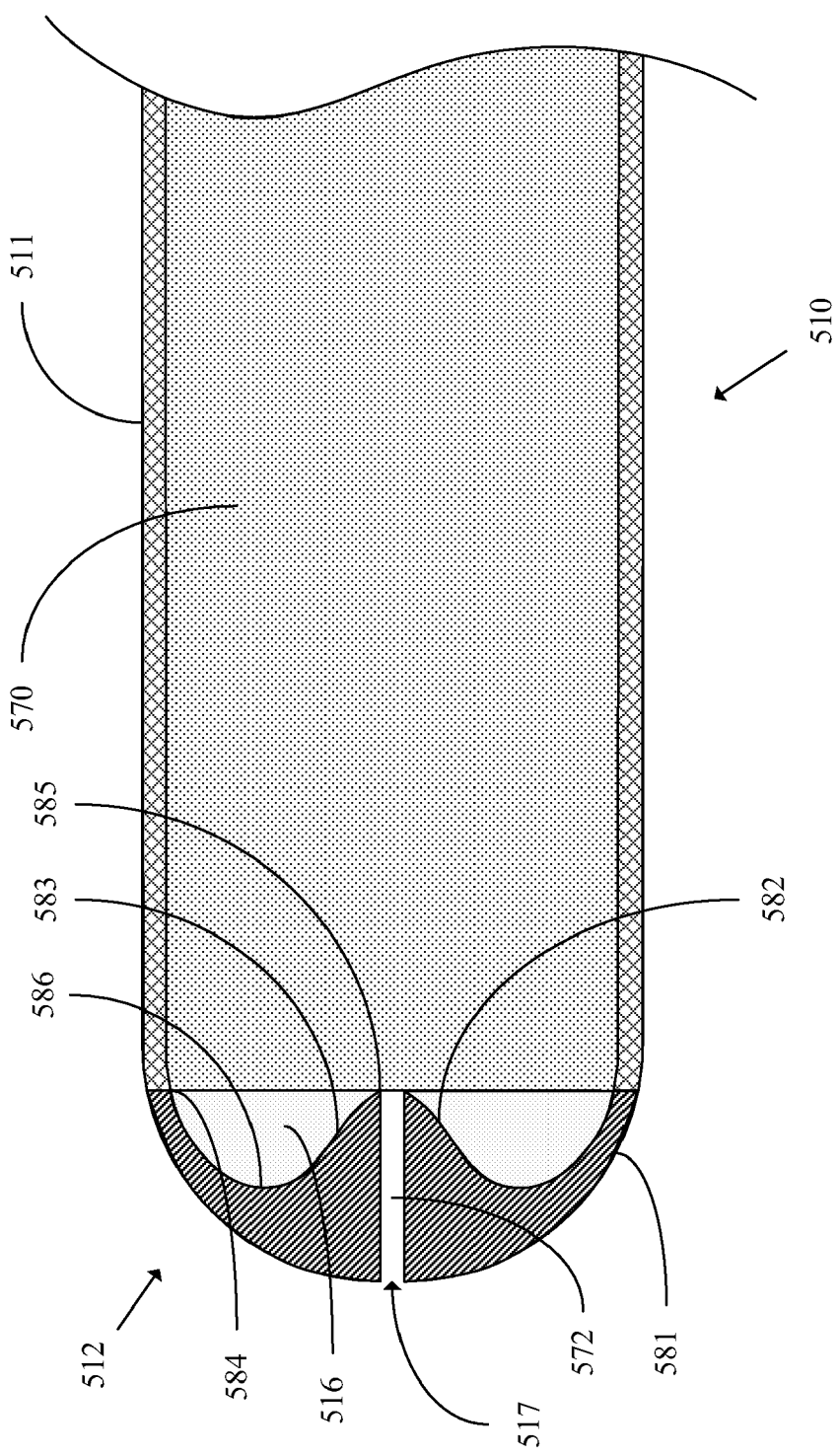

SYSTEMS AND METHODS ALLOWING FOR RESERVOIR AIR BUBBLE MANAGEMENT

CROSS-REFERENCE TO RELATED PATENT APPLICATIONS

Embodiments of the present invention relate to U.S. Provisional Application Ser. No. 60/927,032, filed Apr. 30, 2007, entitled "Needle Inserting, Reservoir Filling, Bubble Management, Fluid Flow Connections and Infusion Medium Delivery Systems and Methods with Same", the contents of which are incorporated by reference herein and which is a basis for a claim of priority.

Embodiments of the present invention relate to PCT International Application No. PCT/US2007/076641, filed Aug. 23, 2007, the contents of which are incorporated by reference herein, and which claims the benefit of U.S. Provisional Application Ser. No. 60/927,032, filed Apr. 30, 2007.

BACKGROUND OF THE INVENTION

1. Field of the Invention

Embodiments of the present invention relate generally to systems and methods with reservoirs and, in specific embodiments, to a system with a reservoir and a plunger that are shaped to limit a presence of air bubbles in a fluidic medium expelled from the reservoir.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have also been configured in implantable devices, which are implanted inside of the body of a patient. External pump type delivery devices include devices designed for use in a stationary location, such as a hospital, a clinic, or the like, and further include devices configured for ambulatory or portable use, such as devices that are designed to be carried by a patient, or the like. External pump type delivery devices may be connected in fluid flow communication to a patient or user, for example, through a suitable hollow tubing. The hollow tubing may be connected to a hollow needle that is designed to pierce the skin of the patient and to deliver a fluidic medium therethrough. Alternatively, the hollow tubing may be connected directly to the patient as through a cannula, or the like.

Examples of some external pump type delivery devices are described in the following references: (i) Published PCT Application WO 01/70307 (PCT/US01/09139), entitled "Exchangeable Electronic Cards for Infusion Devices"; (ii) Published PCT Application WO 04/030716 (PCT/US2003/028769), entitled "Components and Methods for Patient Infusion Device"; (iii) Published PCT Application WO 04/030717 (PCT/US2003/029019), entitled "Dispenser Components and Methods for Infusion Device"; (iv) U.S. Patent Application Pub. No. 2005/0065760, entitled "Method for Advising Patients Concerning Doses Of Insulin"; and (v) U.S. Pat. No. 6,589,229, entitled "Wearable Self-Contained Drug Infusion Device", each of which is incorporated by reference herein in its entirety.

As compared to syringes and insulin pens, pump type delivery devices can be significantly more convenient to a patient, in that doses of insulin may be calculated and delivered automatically to a patient at any time during the day or night. Furthermore, when used in conjunction with glucose sensors or monitors, insulin pumps may be automatically controlled to provide appropriate doses of a fluidic medium at appropriate times of need, based on sensed or monitored levels of blood glucose. As a result, pump type delivery devices have become an important aspect of modern medical treatments of various types of medical conditions, such as diabetes, and the like. As pump technologies improve and doctors and patients become more familiar with such devices, external medical infusion pump treatments are expected to increase in popularity and are expected to increase substantially in number over the next decade.

SUMMARY OF THE DISCLOSURE

Various embodiments of the present invention are directed to limiting a presence of air bubbles in a fluidic medium expelled from a reservoir. In various embodiments, a plunger head within a reservoir is shaped so as to limit a presence of air bubbles in a fluidic medium expelled from the reservoir. Also, in various embodiments, a reservoir is shaped so as to limit a presence of air bubbles in a fluidic medium expelled from the reservoir. In some embodiments, both a reservoir and a plunger head within the reservoir are shaped so as to limit a presence of air bubbles in a fluidic medium expelled from the reservoir.

A plunger head in accordance with an embodiment of the present invention is moveable within a reservoir. In various embodiments, the plunger head is shaped to form a bubble trap region for trapping air bubbles that are in a fluidic medium as the fluidic medium is expelled from the reservoir by the plunger head. In some embodiments, the plunger head has a concave portion that defines the bubble trap region.

In various embodiments, the plunger head includes a body portion, a first protrusion portion protruding from the body portion, and a second protrusion portion protruding from the body portion, where the bubble trap region is located between the first protrusion portion and the second protrusion portion. In some embodiments, the first protrusion portion surrounds at least a portion of the second protrusion portion. Also, in some embodiments, the first protrusion portion extends a first distance from the body portion, the second protrusion portion extends a second distance from the body portion, and the first distance is greater than the second distance. In some embodiments, the second distance is greater than one-fourth of the first distance. Also, in some embodiments, the second protrusion portion includes a cavity for receiving a portion of a needle.

In various embodiments, the plunger head includes a curved surface that defines the bubble trap region, where the curved surface has a first end position, a second end position, and an innermost position. In further embodiments, a depth of the bubble trap region is at least greater than one-half of a width of the bubble trap region from the first end position to the second end position.

A system for delivering a fluidic medium in accordance with an embodiment of the present invention includes a reservoir and a plunger head. In various embodiments, the reservoir includes a reservoir body portion having an interior volume for containing the fluidic medium, and a port in fluid flow communication with the interior volume. Also, in various embodiments, the plunger head is moveable within the reservoir, and the plunger head is shaped to form a bubble trap region for trapping air bubbles that are in the fluidic medium as the fluidic medium is being expelled from the interior volume through the port by the plunger head. In some embodiments, the plunger head has a concave portion that defines the bubble trap region.

In various embodiments, the plunger head includes a body portion, a first protrusion portion protruding from the body portion, and a second protrusion portion protruding from the body portion, where the bubble trap region is located between the first protrusion portion and the second protrusion portion. In some embodiments, the first protrusion portion surrounds at least a portion of the second protrusion portion. In some embodiments, the first protrusion portion extends a first distance from the body portion, the second protrusion portion extends a second distance from the body portion, and the first distance is greater than the second distance. Also, in some embodiments, the second distance is greater than one-fourth of the first distance. In various embodiments, the second protrusion portion is aligned with the port such that when a needle is inserted into the port, an end of the needle is directed toward the second protrusion portion. Also, in various embodiments, the second protrusion portion includes a cavity for receiving a portion of a needle.

In various embodiments, the reservoir further includes a reservoir bubble trap portion having a volume in fluid flow communication with the interior volume for trapping air bubbles that are in the fluidic medium as the fluidic medium is being expelled from the interior volume. In some embodiments, a contour of the first protrusion portion of the plunger head substantially matches an inner contour of the reservoir bubble trap portion. In various embodiments, the first protrusion portion of the plunger head is shaped and positioned such that the first protrusion portion extends at least partially into the volume of the reservoir bubble trap portion when the plunger head is sufficiently advanced within the reservoir. In some embodiments, the first protrusion portion of the plunger head is shaped and positioned such that when the plunger head is fully advanced within the reservoir the first protrusion portion substantially fills the volume of the reservoir bubble trap portion.

In various embodiments, the reservoir is shaped such that in order for the fluidic medium to flow from the volume of the reservoir bubble trap portion to the port, the fluidic medium must flow through the interior volume. In some embodiments, the reservoir includes a material for shunting air bubbles in the fluidic medium away from the port and toward the volume of the reservoir bubble trap portion when the fluidic medium is being expelled from the interior volume. In some embodiments, the reservoir further includes a channel that leads from the interior volume to the port. Also, in some embodiments, the reservoir bubble trap portion includes a first portion that extends from the reservoir body portion away from the interior volume, and a second portion that returns back toward the interior volume, where the reservoir bubble trap portion encircles at least a portion of the channel.

In various embodiments, the system further includes a drive device, a plunger arm, a disposable housing, and a durable housing. In some embodiments, the drive device includes a linkage portion and a motor for moving the linkage portion. In some embodiments, the plunger arm is connected to the plunger head, and the plunger arm has a mating portion for mating with the linkage portion of the drive device. In various embodiments, the disposable housing allows for housing the reservoir and for being secured to a user. Also, in various embodiments, the durable housing allows for housing the motor of the drive device, where the durable housing is configured to be selectively engaged with and disengaged from the disposable housing.

A method in accordance with an embodiment of the present invention allows for expelling a fluidic medium from a reservoir using a plunger head. In various embodiments, the plunger head has a concave portion that defines a bubble trap region. Also, in various embodiments, the method includes expelling the fluidic medium from the reservoir using the plunger head, and trapping, in the bubble trap region defined by the concave portion of the plunger head, air bubbles that are in the fluidic medium as the fluidic medium is being expelled from the reservoir by the plunger head.

A system in accordance with an embodiment of the present invention includes a reservoir and a plunger head. The plunger head is moveable within the reservoir and has a cavity for receiving at least a portion of a needle when the plunger head is sufficiently advanced within the reservoir and the portion of the needle is inserted into the reservoir. In various embodiments, the reservoir has a reservoir body portion and a neck portion. Also, in various embodiments, the plunger head has a plunger body portion and a plunger neck portion and the cavity is in the plunger neck portion.

In various embodiments, the system further includes a seal surrounding at least a part of the plunger body portion, where the seal is in contact with the reservoir body portion of the reservoir when the plunger body portion is within the reservoir body portion of the reservoir. Also, in various embodiments, the system further includes a septum positioned at an end of the neck portion of the reservoir, and the cavity of the plunger neck portion is located in a position such that the cavity receives the portion of the needle when the plunger head is sufficiently advanced within the reservoir and the needle pierces the septum.

In some embodiments, an opening of the cavity of the plunger neck portion is located approximately at a center of an end surface of the plunger head. Also, in some embodiments, a contour of an outer surface of the plunger neck portion substantially matches a contour of an inner surface of the neck portion of the reservoir. In various embodiments, a diameter of an outer surface of the plunger neck portion substantially matches a diameter of an inner surface of the neck portion of the reservoir.

In various embodiments, the reservoir further includes a sloped portion between the reservoir body portion and the neck portion, and the plunger head further includes a plunger sloped portion between the plunger body portion and the plunger neck portion. In some embodiments, the system further includes a septum positioned at an end of the neck portion of the reservoir, and a length of the plunger neck portion from an end of the plunger neck portion to the plunger sloped portion substantially matches a length of the neck portion of the reservoir from the septum to the sloped portion of the reservoir. Also, in some embodiments, the cavity of the plunger neck portion extends into the plunger neck portion a distance that is greater than one-fourth of the length of the plunger neck portion.

In various embodiments, the plunger neck portion is shaped such that the plunger neck portion substantially fills an area within the neck portion of the reservoir when the plunger head is fully advanced within the reservoir. In some embodiments, the system further includes a drive device including a linkage portion and a motor for moving the linkage portion, and a plunger arm connected to the plunger head, where the plunger arm has a mating portion for mating with the linkage portion of the drive device. Also, in some embodiments, the system further includes a disposable housing for housing the reservoir and for being secured to a user, and a durable housing for housing the motor of the drive device, where the durable housing is configured to be selectively engaged with and disengaged from the disposable housing.

A method in accordance with an embodiment of the present invention includes piercing a septum of a reservoir with a needle, and moving a plunger head within the reservoir such that at least a portion of the needle is received within a cavity of the plunger head. In some embodiments, the moving includes moving the plunger head within the reservoir such that a plunger neck portion of the plunger head extends into a neck portion of the reservoir. Also, in some embodiments, the moving includes moving the plunger head within the reservoir such that a portion of the plunger head contacts a portion of the septum.

In various embodiments, the method further includes retracting the plunger head within the reservoir to allow a fluidic medium to flow through the needle and into the reservoir. Also, in various embodiments, the method further includes removing the needle from the reservoir, piercing the septum of the reservoir with another needle, and moving the plunger head within the reservoir until at least a portion of the another needle is received within the cavity of the plunger head, so as to expel the fluidic medium from the reservoir through the another needle.

A system in accordance with another embodiment of the present invention includes a reservoir. The reservoir includes a reservoir body portion, a port, and a bubble trap portion. The reservoir body portion has an interior volume for containing a fluidic medium. The port is in fluid flow communication with the interior volume. The bubble trap portion has a volume in fluid flow communication with the interior volume for trapping air bubbles that are in the fluidic medium as the fluidic medium is being expelled from the interior volume.

In various embodiments, the port is located to a particular side of the interior volume, and the bubble trap portion is located to the particular side of the interior volume. In some embodiments, the bubble trap portion has a first portion that extends from the reservoir body portion away from the interior volume, and a second portion that returns back toward the interior volume. In various embodiments, the reservoir body portion and the bubble trap portion are a single seamless unit.

In some embodiments, the bubble trap portion has a first portion that extends from the reservoir body portion away from the interior volume, and a second portion that extends from the first portion toward the interior volume. Also, in some embodiments, the bubble trap portion includes a curved surface, and the curved surface has a first end region, a second end region, and a middle region between the first end region and the second end region. In further embodiments, the first end region and the second end region are closer to the interior volume than the middle region. Also, in further embodiments, the first end region is in contact with the reservoir body portion, and the second end region is located adjacent to the interior volume of the reservoir body portion.

In various embodiments, the bubble trap portion is shaped approximately as a semi-toroid. Also, in various embodiments, a surface of the bubble trap portion that is in contact with the fluidic medium when the fluidic medium is in the volume of the bubble trap portion is approximately U-shaped. In some embodiments, the bubble trap portion includes a first surface that defines an edge of the volume of the bubble trap portion, and a second surface that defines another edge of the volume of the bubble trap portion, where the second surface is positioned at an angle with respect to the first surface. In further embodiments, the angle between the first surface and the second surface is less than 90 degrees. Also, in further embodiments, the first surface is planar with respect to an inner surface of the reservoir body portion.

In various embodiments, the port is located to a particular side of the interior volume, and a first portion of the bubble trap portion extends from the reservoir body portion to the particular side. In further embodiments, the first portion is curved, and a second portion of the bubble trap portion extends from an end of the first portion toward the interior volume. In some embodiments, the reservoir is shaped such that in order for the fluidic medium to flow from the volume of the bubble trap portion to the port, the fluidic medium must flow through the interior volume. Also, in some embodiments, the reservoir further includes a channel that leads from the interior volume to the port, and the bubble trap portion encircles at least a portion of the channel.

In various embodiments, the system further includes a plunger head having a plunger body portion and a plunger protruding portion, where the plunger head is moveable within the reservoir. In further embodiments, a contour of the plunger protruding portion substantially matches an inner contour of the bubble trap portion. In some embodiments, the plunger protruding portion has a size such that when the plunger head is fully advanced within the reservoir the plunger protruding portion substantially fills the volume of the bubble trap portion. Also, in some embodiments, the plunger protruding portion fills less than all of the volume of the bubble trap portion when the plunger head is fully advanced within the reservoir, so that one or more air pockets for holding air exist between the plunger protruding portion and an inner surface of the bubble trap portion when the plunger head is fully advanced within the reservoir.

In various embodiments, the plunger protruding portion extends at least partially into the volume of the bubble trap portion when the plunger head is sufficiently advanced within the reservoir. Also, in various embodiments the system further includes a plunger head moveable within the reservoir, where the plunger head has a relief for receiving at least a portion of a needle when the plunger head is sufficiently advanced within the reservoir and the portion of the needle is inserted into the reservoir. In some embodiments, the reservoir includes at least one of a hydrophobic material and a hydrophilic material on at least part of a surface of the bubble trap portion. Also, in some embodiments, the reservoir includes a material for shunting air bubbles in the fluidic medium away from the port and toward the volume of the bubble trap portion when the fluidic medium is being expelled from the interior volume.

In various embodiments, the system further includes a plunger head moveable within the reservoir, a drive device including a linkage portion and a motor for moving the linkage portion, and a plunger arm connected to the plunger head, where the plunger arm has a mating portion for mating with the linkage portion of the drive device. Also, in various embodiments, the system includes a disposable housing for housing the reservoir and for being secured to a user, and a durable housing for housing the motor of the drive device, where the durable housing is configured to be selectively engaged with and disengaged from the disposable housing.

BRIEF DESCRIPTION OF THE DRAWINGS

FIG. 12A illustrates a cross-sectional view of a system in accordance with an embodiment of the present invention;

FIG. 12B illustrates a cross-sectional view of a reservoir in accordance with an embodiment of the present invention;

DETAILED DESCRIPTION OF PREFERRED EMBODIMENTS

Figure 1:
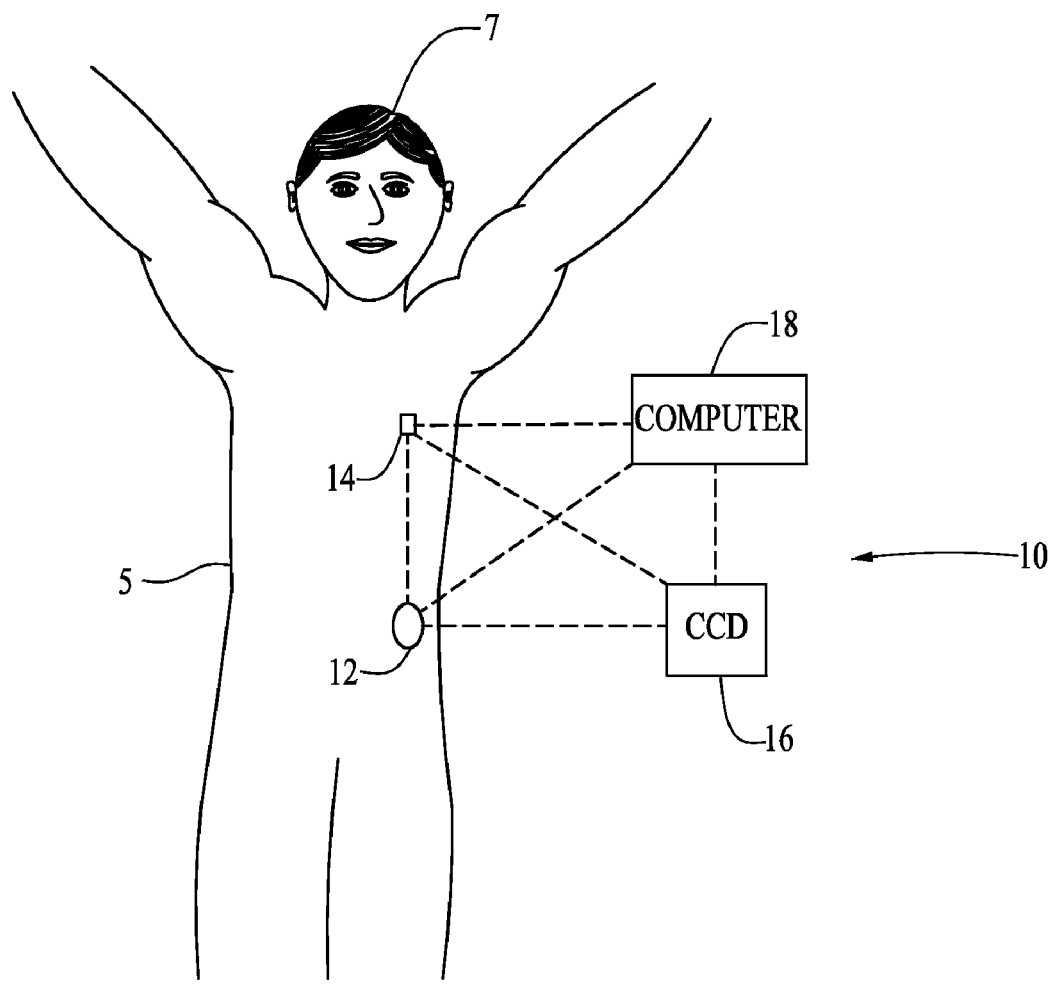
FIG. 1 illustrates a generalized representation of a system in accordance with an embodiment of the present invention.

FIG. 1 illustrates a generalized representation of a system 10 in accordance with an embodiment of the present invention. The system 10 includes a delivery device 12. The system 10 may further include a sensing device 14, a command control device (CCD) 16, and a computer 18. In various embodiments, the delivery device 12 and the sensing device 14 may be secured at desired locations on the body 5 of a patient or user 7. The locations at which the delivery device 12 and the sensing device 14 are secured to the body 5 of the user 7 in FIG. 1 are provided only as representative, non-limiting, examples.

The delivery device 12 is configured to deliver a fluidic medium to the body 5 of the user 7. In various embodiments, the fluidic medium includes a liquid, a fluid, a gel, or the like. In some embodiments, the fluidic medium includes a medicine or a drug for treating a disease or a medical condition. For example, the fluidic medium may include insulin for treating diabetes, or may include a drug for treating pain, cancer, a pulmonary disorder, HIV, or the like. In some embodiments, the fluidic medium includes a nutritional supplement, a dye, a tracing medium, a saline medium, a hydration medium, or the like.

The sensing device 14 includes a sensor, a monitor, or the like, for providing sensor data or monitor data. In various embodiments, the sensing device 14 may be configured to sense a condition of the user 7. For example, the sensing device 14 may include electronics and enzymes reactive to a biological condition, such as a blood glucose level, or the like, of the user 7. In various embodiments, the sensing device 14 may be secured to the body 5 of the user 7 or embedded in the body 5 of the user 7 at a location that is remote from the location at which the delivery device 12 is secured to the body 5 of the user 7. In various other embodiments, the sensing device 14 may be incorporated within the delivery device 12.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver the fluidic medium to the body 5 of the user 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. Also, in various embodiments, the delivery device 12 and/or the sensing device 14 may be configured to transmit data to the CCD 16 and/or the computer 18 for display or processing of the data by the CCD 16 and/or the computer 18. Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same", all of which are incorporated herein by reference in their entirety.

Figure 2:
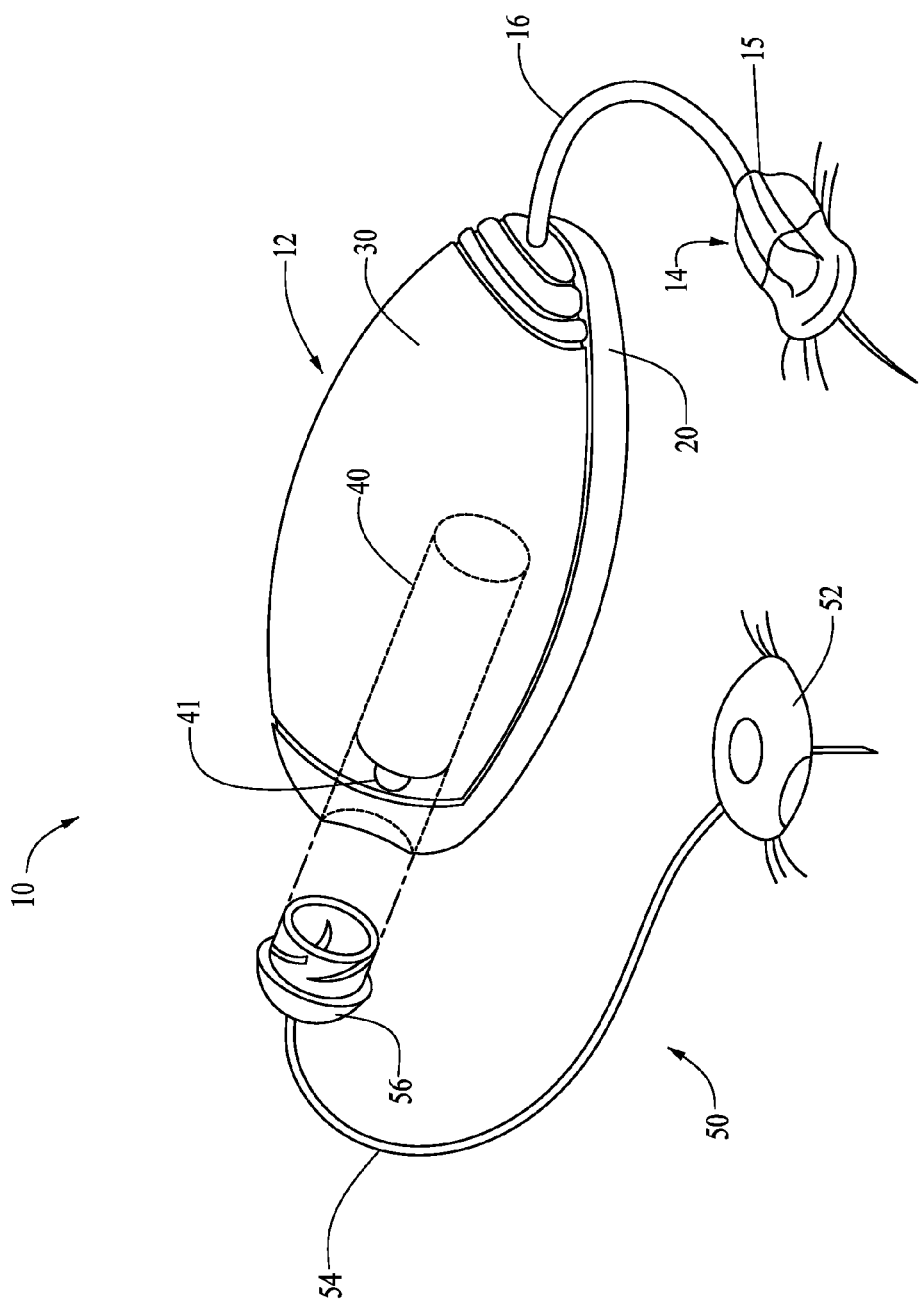
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention includes a disposable housing 20, a durable housing 30, and a reservoir 40. The delivery device 12 may further include an infusion path 50.

Elements of the delivery device 12 that ordinarily contact the body of a user or that ordinarily contact a fluidic medium during operation of the delivery device 12 may be considered as a disposable portion of the delivery device 12. For example, a disposable portion of the delivery device 12 may include the disposable housing 20 and the reservoir 40. The disposable portion of the delivery device 12 may be recommended for disposal after a specified number of uses.

On the other hand, elements of the delivery device 12 that do not ordinarily contact the body of the user or the fluidic medium during operation of the delivery device 12 may be considered as a durable portion of the delivery device 12. For example, a durable portion of the delivery device 12 may include the durable housing 30, electronics (not shown in FIG. 2), and a drive device having a motor and drive linkage (not shown in FIG. 2), and the like. Elements of the durable housing portion of the delivery device 12 are typically not contaminated from contact with the user or the fluidic medium during normal operation of the delivery device 12 and, thus, may be retained for re-use with replaced disposable portions of the delivery device 12.

In various embodiments, the disposable housing 20 supports the reservoir 40 and has a bottom surface (facing downward and into the page in FIG. 2) that is configured to secure to the body of a user. An adhesive may be employed at an interface between the bottom surface of the disposable housing 20 and the skin of a user, so as to adhere the disposable housing 20 to the skin of the user. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the skin of the user.

The reservoir 40 is configured for containing or holding a fluidic medium, such as, but not limited to insulin. In various embodiments, the reservoir 40 includes a hollow interior volume for receiving the fluidic medium, such as, but not limited to, a cylinder-shaped volume, a tubular-shaped volume, or the like. In some embodiments, the reservoir 40 may be provided as a cartridge or canister for containing a fluidic medium. In various embodiments, the reservoir 40 is able to be refilled with a fluidic medium.

The reservoir 40 may be supported by the disposable housing 20 in any suitable manner. For example, the disposable housing 20 may be provided with projections or struts (not shown), or a trough feature (not shown), for holding the reservoir 40. In some embodiments, the reservoir 40 may be supported by the disposable housing 20 in a manner that allows the reservoir 40 to be removed from the disposable housing 20 and replaced with another reservoir. Alternatively, or in addition, the reservoir 40 may be secured to the disposable housing 20 by a suitable adhesive, a strap, or other coupling structure.

In various embodiments, the reservoir 40 includes a port 41 for allowing a fluidic medium to flow into and/or flow out of the interior volume of the reservoir 40. In some embodiments, the infusion path 50 includes a connector 56, a tube 54, and a needle apparatus 52. The connector 56 of the infusion path 50 may be connectable to the port 41 of the reservoir 40. In various embodiments, the disposable housing 20 is configured with an opening near the port 41 of the reservoir 40 for allowing the connector 56 of the infusion path 50 to be selectively connected to and disconnected from the port 41 of the reservoir 40.

In various embodiments, the port 41 of the reservoir 40 is covered with or supports a septum (not shown in FIG. 2), such as a self-sealing septum, or the like. The septum may be configured to prevent a fluidic medium from flowing out of the reservoir 40 through the port 41 when the septum is not pierced. Also, in various embodiments, the connector 56 of the infusion path 50 includes a needle for piercing the septum covering the port 41 of the reservoir 40 so as to allow the fluidic medium to flow out of the interior volume of the reservoir 40. Examples of needle/septum connectors can be found in U.S. patent application Ser. No. 10/328,393, filed Dec. 22, 2003, entitled "Reservoir Connector", which is incorporated herein by reference in its entirety. In other alternatives, non-septum connectors such as Luer locks, or the like may be used. In various embodiments, the needle apparatus 52 of the infusion path 50 includes a needle that is able to puncture the skin of a user. Also, in various embodiments, the tube 54 connects the connector 56 with the needle apparatus 52 and is hollow, such that the infusion path 50 is able to provide a path to allow for the delivery of a fluidic medium from the reservoir 40 to the body of a user.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features, that allow the two parts to easily connect together, by manually pressing the two housings together, by twist or threaded connection, or other suitable manner of connecting the parts that is well known in the mechanical arts. In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20, so as to provide a seal against water entering between the durable housing 30 and the disposable housing 20.

The durable housing 30 of the delivery device 12 may support a drive device (not shown in FIG. 2), including a motor and a drive device linkage portion, for applying a force to the fluidic medium within the reservoir 40 to force the fluidic medium out of the reservoir 40 and into an infusion path, such as the infusion path 50, for delivery to a user. For example, in some embodiments, an electrically driven motor may be mounted within the durable housing 30 with appropriate linkage for operatively coupling the motor to a plunger arm (not shown in FIG. 2) connected to a plunger head (not shown in FIG. 2) that is within the reservoir 40 and to drive the plunger head in a direction to force the fluidic medium out of the port 41 of the reservoir 40 and to the user. Also, in some embodiments, the motor may be controllable to reverse direction so as to move the plunger arm and the plunger head to cause fluid to be drawn into the reservoir 40 from a patient. The motor may be arranged within the durable housing 30 and the reservoir 40 may be correspondingly arranged on the disposable housing 20, such that the operable engagement of the motor with the plunger head, through the appropriate linkage, occurs automatically upon the user connecting the durable housing 30 with the disposable housing 20 of the delivery device 12. Further examples of linkage and control structures may be found in U.S. patent application Ser. No. 09/813,660, filed Mar. 21, 2001, entitled "Control Tabs for Infusion Devices and Methods of Using the Same", which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user, a greater level of user comfort may be achieved when the disposable housing 20 is secured to the skin of the user. Also, a flexible disposable housing 20 may result in an increase in site options on the body of the user at which the disposable housing 20 may be secured.

In the embodiment illustrated in FIG. 2, the delivery device 12 is connected to the sensing device 14 through a connection element 16 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

The sensor 15 may be an external sensor that secures to the skin of a user or, in other embodiments, may be an implantable sensor that is located in an implant site within the body of the user. In further alternatives, the sensor may be included with as a part or along side the infusion cannula and/or needle, such as for example as shown in U.S. patent application Ser. No. 11/149,119, filed Jun. 8, 2005, entitled "Dual Insertion Set", which is incorporated herein by reference in its entirety. In the illustrated example of FIG. 2, the sensor 15 is an external sensor having a disposable needle pad that includes a needle for piercing the skin of the user and enzymes and/or electronics reactive to a biological condition, such as blood glucose level or the like, of the user. In this manner, the delivery device 12 may be provided with sensor data from the sensor 15 secured to the user at a site remote from the location at which the delivery device 12 is secured to the user.

While the embodiment shown in FIG. 2 includes a sensor 15 connected by the connection element 16 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic medium delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user.

Figure 3:
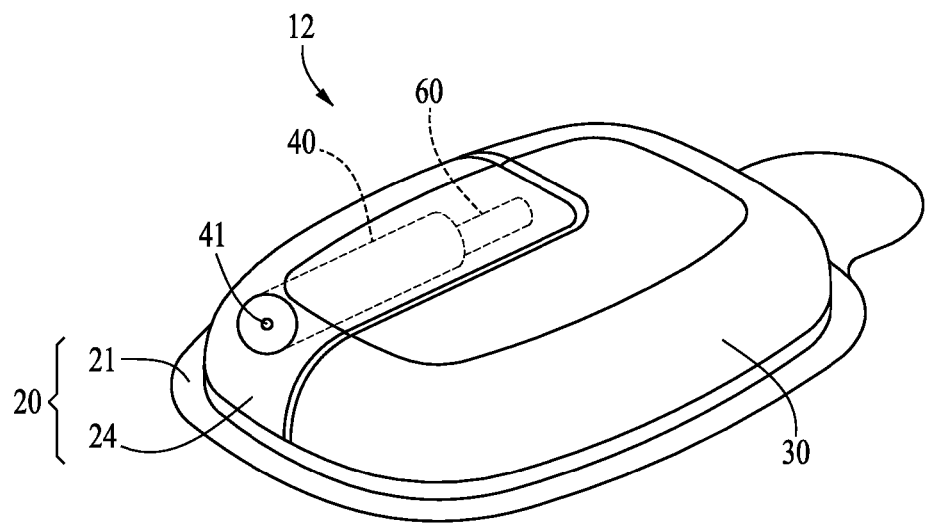
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir 40, the delivery device 12 in the embodiment of FIG. 3 provides for the durable housing 30 to secure to the disposable housing 20 without covering the reservoir 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 is configured to be secured to the body of a user. The reservoir retaining portion 24 of the disposable housing 20 is configured to house the reservoir 40. The reservoir retaining portion 24 of the disposable housing 20 may be configured to have an opening to allow for the port 41 of the reservoir 40 to be accessed from outside of the reservoir retaining portion 24 while the reservoir 40 is housed in the reservoir retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir 40.

Figure 4:
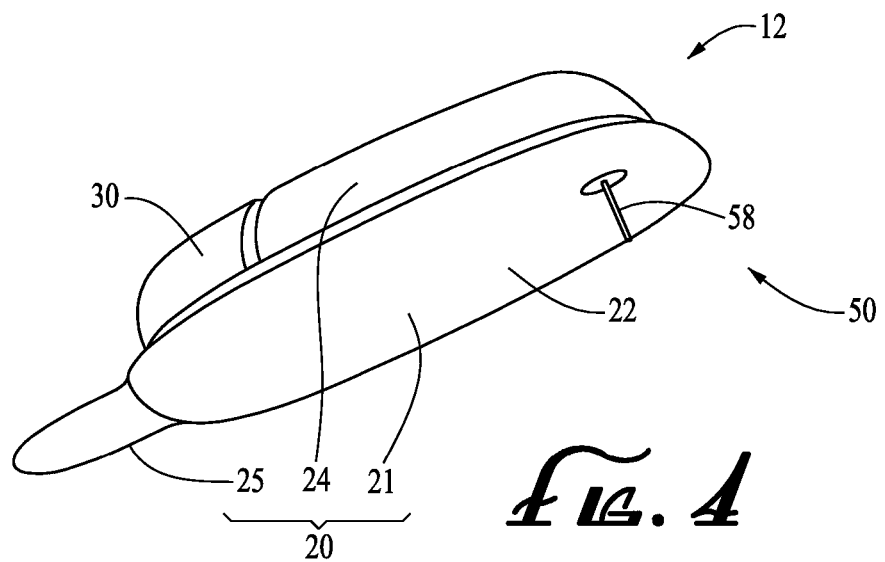
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir retaining portion 24, and a peelable cover layer 25. The peelable cover layer 25 may cover an adhesive material on the bottom surface 22 of the base 21. The peelable cover layer 25 may be configured to be peelable by a user to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user under the base 21, when extended. In this manner, the needle 58 may be used to pierce the skin of the user and deliver a fluidic medium to the user.

Alternatively, the needle 58 may be extended through a hollow cannula (not shown in FIG. 4), such that upon piercing the skin of the user with the needle 58, an end of the hollow cannula is guided through the skin of the user by the needle 58. Thereafter, the needle 58 may be removed, leaving the hollow cannula in place, with one end of the cannula located within the body of the user and the other end of the cannula in fluid flow connection with the fluidic medium within the reservoir 40, to convey pumped infusion media from the reservoir 40 to the body of the user.

Figure 5A:
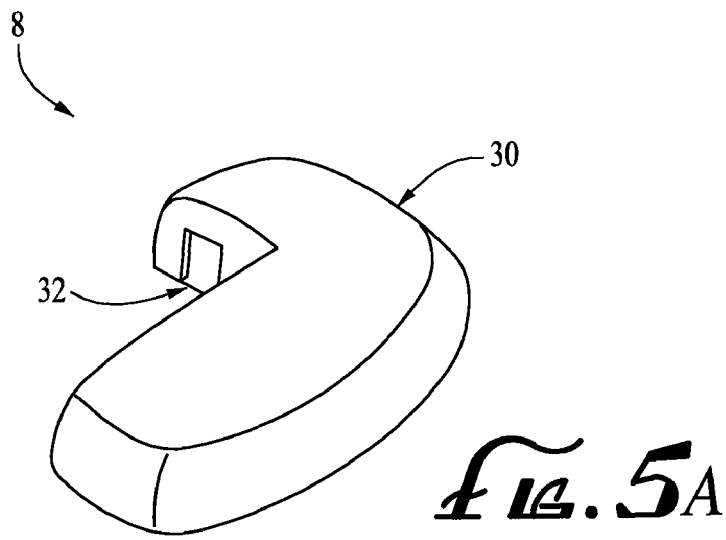
FIG. 5A illustrates a durable portion of a delivery device in accordance with an embodiment of the present invention.
Figure 5B:
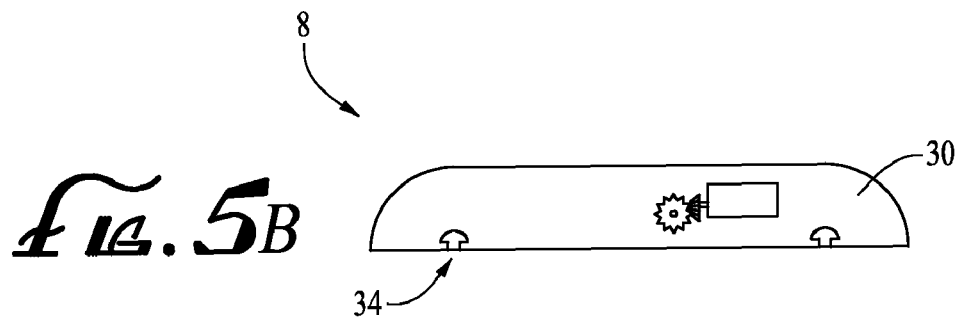
FIG. 5B illustrates a section view of a durable portion of a delivery device in accordance with an embodiment of the present invention.
Figure 5C:
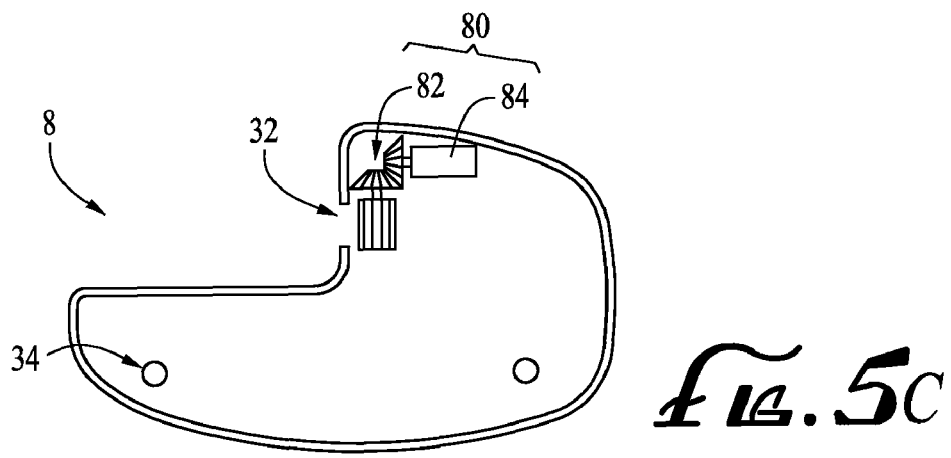
FIG. 5C illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 includes the durable housing 30, and a drive device 80. The drive device 80 includes a motor 84 and a drive device linkage portion 82. In various embodiments, the durable housing 30 may include an interior volume for housing the motor 84, the drive device linkage portion 82, other electronic circuitry, and a power source (not shown in FIGS. 5A, 5B, and 5C). Also, in various embodiments, the durable housing 30 is configured with an opening 32 for receiving a plunger arm 60 (refer to FIG. 3). Also, in various embodiments, the durable housing 30 may include one or more connection members 34, such as tabs, insertion holes, or the like, for connecting with the base 21 of the disposable housing 20 (refer to FIG. 3).

Figure 6A:
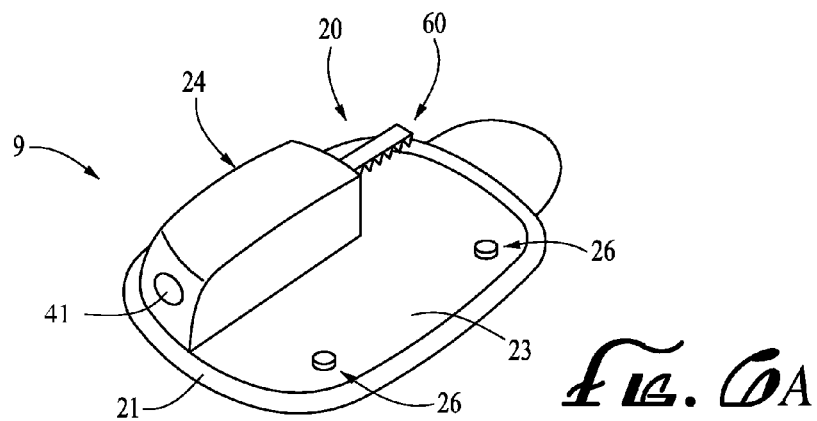
FIG. 6A illustrates a disposable portion of a delivery device in accordance with an embodiment of the present invention.
Figure 6B:
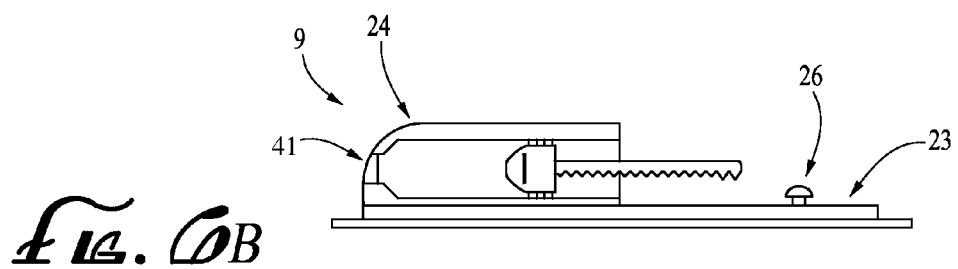
FIG. 6B illustrates a section view of a disposable portion of a delivery device in accordance with an embodiment of the present invention.
Figure 6C:
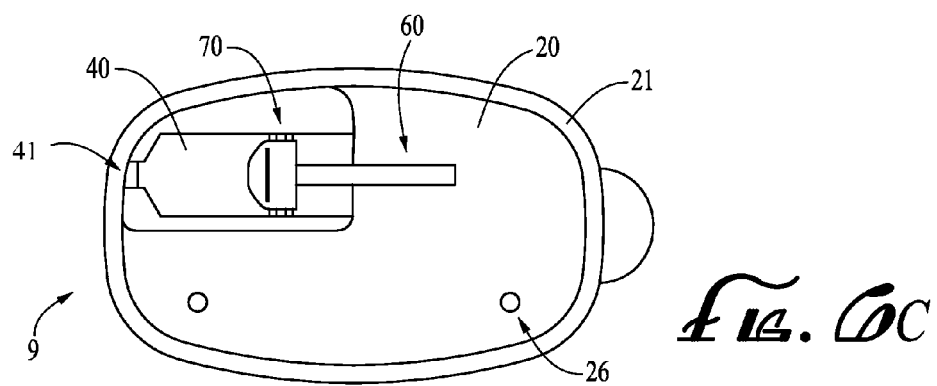
FIG. 6C illustrates a section view of a disposable portion of a delivery device in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir 40, the plunger arm 60, and a plunger head 70. In some embodiments, the disposable housing 20 includes the base 21 and the reservoir retaining portion 24. In various embodiments, the base 21 includes a top surface 23 having one or more connection members 26, such as tabs, grooves, or the like, for allowing connections with the one or more connection members 34 of embodiments of the durable housing 30 (refer to FIG. 5B).

In various embodiments, the reservoir 40 is housed within the reservoir retaining portion 24 of the disposable housing 20, and the reservoir 40 is configured to hold a fluidic medium. Also, in various embodiments, the plunger head 70 is disposed at least partially within the reservoir 40 and is moveable within the reservoir 40 to allow the fluidic medium to fill into the reservoir 40 and to force the fluidic medium out of the reservoir 40. In some embodiments, the plunger arm 60 is connected to or is connectable to the plunger head 70. Also, in some embodiments, a portion of the plunger arm 60 extends to outside of the reservoir retaining portion 24 of the disposable housing 20. In various embodiments, the plunger arm 60 has a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82 and, thus, move the plunger arm 60 to cause the plunger head 70 to move within the reservoir 40. When the interior volume of the reservoir 40 is filled with a fluidic medium and an infusion path is provided from the reservoir 40 to the body of a user, the plunger head 70 may be moved within the reservoir 40 to force the fluidic medium from the reservoir 40 and into the infusion path, so as to deliver the fluidic medium to the body of the user.

In various embodiments, once the reservoir 40 has been sufficiently emptied or otherwise requires replacement, a user may simply remove the durable housing 30 from the disposable housing 20, and replace the disposable portion 9, including the reservoir 40, with a new disposable portion having a new reservoir. The durable housing 30 may be connected to the new disposable housing of the new disposable portion, and the delivery device including the new disposable portion may be secured to the skin of a user. In various other embodiments, rather than replacing the entire disposable portion 9 every time the reservoir 40 is emptied, the reservoir 40 may be refilled with a fluidic medium. In some embodiments, the reservoir 40 may be refilled while remaining within the reservoir retaining portion 24 (refer to FIG. 6B) of the disposable housing 20. Also, in various embodiments, the reservoir 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 includes reservoir status circuitry (not shown), and the reservoir 40 includes reservoir circuitry (not shown). In various embodiments, the reservoir circuitry stores information such as, but not limited to, at least one of (i) an identification string identifying the reservoir 40; (ii) a manufacturer of the reservoir 40; (iii) contents of the reservoir 40; and (iv) an amount of contents in the reservoir 40. In some embodiments, the delivery device 12 includes the reservoir status circuitry (not shown), and the reservoir status circuitry is configured to read data from the reservoir circuitry when the reservoir 40 is inserted into the disposable portion 9.

In various embodiments, the reservoir status circuitry is further configured to store data to the reservoir circuitry after at least some of the contents of the reservoir 40 have been transferred out of the reservoir 40, so as to update information in the reservoir circuitry related to an amount of contents still remaining in the reservoir 40. In some embodiments, the reservoir status circuitry is configured to store data to the reservoir circuitry, so as to update information in the reservoir circuitry related to an amount of contents still remaining in the reservoir 40, when the reservoir 40 is inserted into the disposable portion 9. In some embodiments, the delivery device 12 includes the reservoir status circuitry (not shown) and the reservoir 40 includes the reservoir circuitry (not shown), and the reservoir status circuitry selectively inhibits use of the delivery device 12 or selectively provides a warning signal based on information read by the reservoir status circuitry from the reservoir circuitry.

Figure 7A:
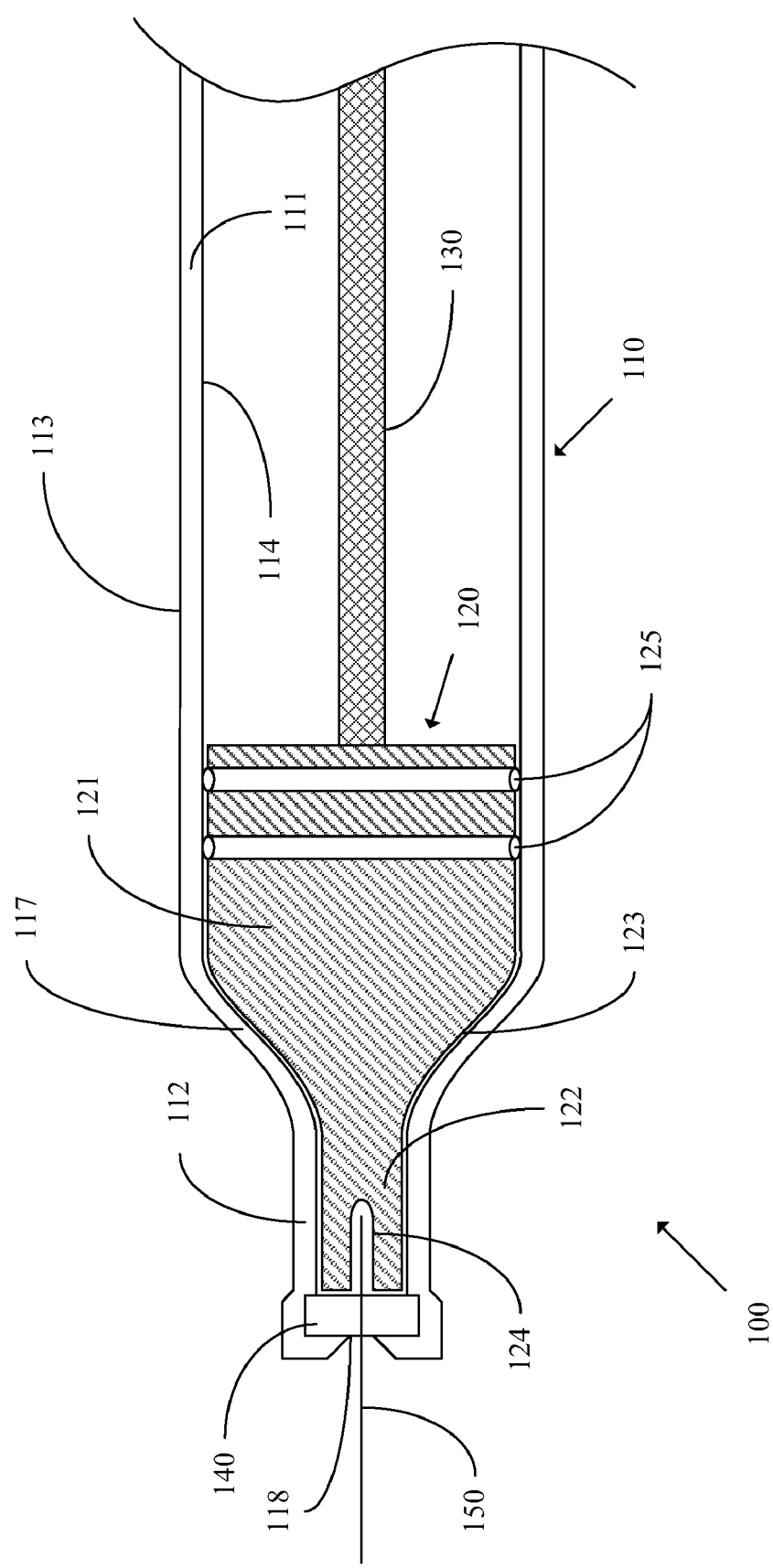
FIG. 7A illustrates a cross-sectional view of a system in accordance with an embodiment of the present invention.

FIG. 7A illustrates a cross-sectional view of a system 100 in accordance with an embodiment of the present invention. The system 100 includes a reservoir 110, a plunger head 120, a plunger arm 130, and a septum 140. In various embodiments, the system 100 further includes a needle 150. In some embodiments, the system 100 may further include similar elements as elements of embodiments of the delivery device 12 (refer to FIGS. 2 and 3), in which case the reservoir 110 would correspond to the reservoir 40 (refer to FIGS. 2, 3, and 6C). In various embodiments, the reservoir 110 may be made of a material, such as but not limited to a suitable metal, plastic, ceramic, glass, composite material, or the like. In various embodiments, the plunger head 120 may be made of a suitably rigid material such as, but not limited to, metal, plastic, ceramic, glass, composite material, or the like. In various other embodiments, the plunger head 120 may be made of a compressible material such as, but not limited to, an elastically compressible plastic, rubber, silicone, or the like.

In various embodiments, the reservoir 110 includes a reservoir body portion 111, a body headspace or neck portion 112, and a curved or sloped portion 117 that connects the reservoir body portion 111 and the neck portion 112. The reservoir 110 has an outer surface 113 and an inner surface 114. The inner surface 114 of the reservoir 110 defines a hollow interior of the reservoir 110, and the hollow interior of the reservoir 110 is able to contain a fluidic medium. The reservoir 110 further includes a port 118 at an end of the neck portion 112, through which the fluidic medium may be filled into or expelled from the hollow interior of the reservoir 110. The reservoir body portion 111 of the reservoir 110 may have any suitable shape and may have, for example, a cylinder shape, a tube shape, a barrel shape, a spherical shape, a shape with a rectangular cross-section, or the like. Similarly, the neck portion 112 of the reservoir 110 may have any suitable shape and may have, for example, a cylinder shape, a tube shape, a barrel shape, a spherical shape, a shape with a rectangular cross-section, or the like.

The plunger head 120 is located within the reservoir 110, and is moveable in an axial direction of the reservoir 110, to expand or contract an interior volume of the reservoir 110 in which a fluidic medium may be contained. The plunger head 120 is connected to the plunger arm 130, such that movement of the plunger arm 130 in the axial direction of the reservoir 110 causes movement of the plunger head 120 in the axial direction of the reservoir 110. The plunger head 120 includes a plunger body portion 121, a plunger headspace or neck portion 122, and a plunger curved or sloped portion 123 that connects the plunger body portion 121 and the plunger neck portion 122. In various embodiments, the plunger head 120 further includes one or more seals 125 that surround a portion of the plunger body portion 121.

The plunger body portion 121 is shaped such that a contour of an outer surface of the plunger body portion 121 substantially matches or is substantially the same as a contour of an inner surface of the reservoir body portion 111 of the reservoir 110. In various embodiments, the plunger body portion 121 has a diameter that is slightly smaller than a diameter of the inner surface of the reservoir body portion 111 of the reservoir 110, such that the plunger head 120 is able to slide within the reservoir 110. In some embodiments, the one or more seals 125 on the plunger body portion 121 are in contact with the inner surface of the reservoir body portion 111 of the reservoir 110 when the plunger head 120 is within the reservoir 110.

The plunger neck portion 122 is shaped such that a contour of an outer surface of the plunger neck portion 122 substantially matches or is substantially the same as a contour of an inner surface of the neck portion 112 of the reservoir 110. In various embodiments, the plunger neck portion 122 has a diameter that is slightly smaller than a diameter of the inner surface of the neck portion 112 of the reservoir 110, such that the plunger neck portion 122 is able to slide within the neck portion 112 of the reservoir 110. In some embodiments, a diameter of an outer surface of the plunger neck portion 122 closely matches or substantially matches a diameter of an inner surface of the neck portion 112 of the reservoir 110. Also, in some embodiments, the plunger neck portion 122 is shaped such that the plunger neck portion 122 substantially fills an area within the neck portion 112 of the reservoir 110 when the plunger head 120 is fully advanced within the reservoir 110. The plunger sloped portion 123 is shaped such that a contour of an outer surface of the plunger sloped portion 123 substantially matches or is substantially the same as a contour of an inner surface of the sloped portion 117 of the reservoir 110.

The septum 140 is located at the port 118 of the reservoir 110. The septum 140 may be formed of a suitable material, such as, but not limited to, rubber, silicone rubber, polyurethane, or other materials that may be pierced by a needle and form a seal around a needle. The neck portion 112 has a certain length from an end of the sloped portion 117 to the septum 140. In various embodiments, the plunger neck portion 122 has a length that is substantially the same as the certain length of the neck portion 112 of the reservoir 110. In some such embodiments, the plunger neck portion 122 is able to extend substantially all of the way into the neck portion 112 of the reservoir 110 when the plunger head 120 is fully advanced within the reservoir 110. Thus, in some embodiments, an end of the plunger neck portion 122 may be close to or in contact with the septum 140 when the plunger head 120 is fully advanced within the reservoir 110. In various embodiments, a length of the plunger neck portion 122 from an end of the plunger neck portion 122 to the plunger sloped portion 123 substantially matches a length of the neck portion 112 of the reservoir 110 from the septum 140 to the sloped portion 117 of the reservoir 110.

The septum 140 is able to be pierced by the needle 150, such as to allow for a fluidic medium to be passed through the needle 150 and into the hollow interior of the reservoir 110. In various embodiments, the plunger head 120 includes a hole or a channel or a relief or a cavity 124 that is able to accommodate a portion of the needle 150 when the plunger head 120 is sufficiently advanced within the reservoir 110 and the septum 140 is pierced by the needle 150. The cavity 124 may have any suitable shape for accommodating a portion of the needle 150, and may have, for example, a cylindrical shape, a tube shape with a half-sphere bottom, a shape with a rectangular cross-section, or the like. In various embodiments, a diameter of the cavity 124 is larger than a diameter of the needle 150, such that an end of the needle 150 is able to fit within the cavity 124.

In various embodiments, the cavity 124 is in the plunger neck portion 122 of the plunger head 120. In some embodiments, a length of the cavity 124 in the plunger neck portion 122 in a direction from the septum 140 toward the plunger body portion 121 is greater than one-quarter of a length of the plunger neck portion 122. Also, in some embodiments, the cavity 124 is positioned at a center of an end surface of the plunger neck portion 122. In some embodiments, the cavity 124 is positioned off-center at an end surface of the plunger neck portion 122. In various embodiments, an end of the neck portion 112 of the reservoir 110 partially covers the septum 140, such that the needle 150 may only pierce the septum 140 in a location that is aligned with the cavity 124 of the plunger head 120.

Figure 8:
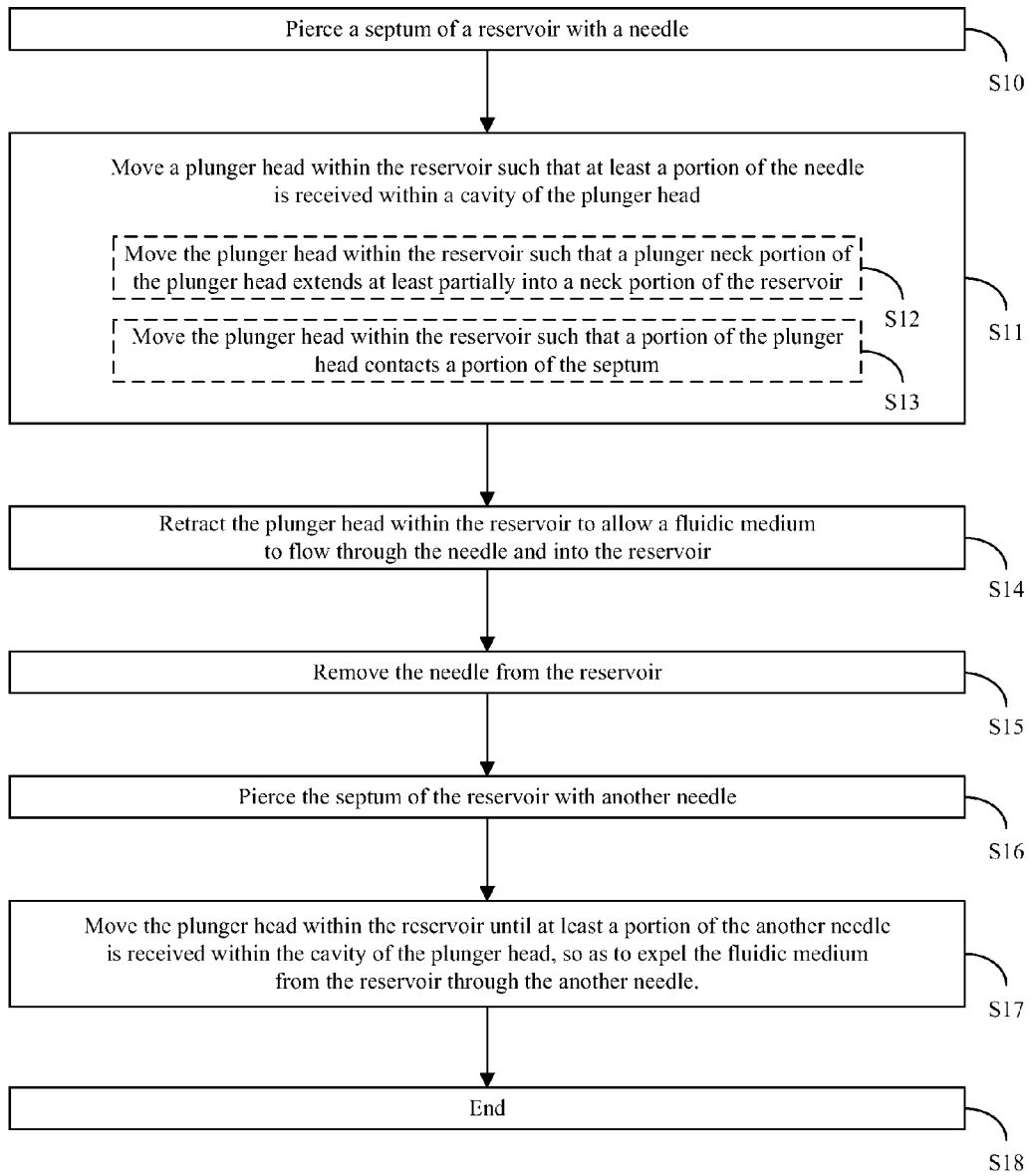
FIG. 8 illustrates a flowchart for a method in accordance with an embodiment of the present invention.

FIG. 8 illustrates a flowchart for a method in accordance with an embodiment of the present invention. With reference to FIGS. 7A and 8, in various embodiments the method of FIG. 8 allows for filling the reservoir 110 with a fluidic medium and for expelling the fluidic medium from the reservoir 110. In S10, the septum 140 of the reservoir 110 is pierced with the needle 150, and the method continues to S11.

In S11, the plunger head 120 is advanced within the reservoir 110, such that at least a portion of the needle 150 is received within the cavity 124 of the plunger head 120. For example, the plunger arm 130 may be driven by a motor (not shown in FIG. 7A) or by a force applied by a user to advance the plunger head 120 within the reservoir 110. In various embodiments, moving the plunger head 120 includes moving the plunger head 120 within the reservoir 110 such that the plunger neck portion 122 extends at least partially into the neck portion 112 of the reservoir 110 (S12). Also, in various embodiments, moving the plunger head 120 includes moving the plunger head 120 within the reservoir 110 such that a portion of the plunger head 120 contacts a portion of the septum 140 (S13). In some embodiments, S10 and S11 are performed in a reverse order, such that the plunger head 120 is moved and then the septum 140 is pierced with the needle 150.

When the plunger head 120 is sufficiently advanced within the reservoir 110, a portion of the needle 150 may extend into the cavity 124 of the plunger neck portion 122, which may allow the plunger neck portion 122 to extend substantially all the way to the septum 140. As a consequence, a presence of air pockets between an end of the plunger head 120 and the septum 140 is able to be substantially limited or eliminated when the plunger head 120 is fully advanced within the reservoir 110. Reducing air pockets between the plunger head 120 and the septum 140 prior to filling the reservoir 110 is beneficial, because it limits an amount of air bubbles that subsequently enter the fluidic medium when the fluidic medium is drawn into the reservoir 110.

Figure 7B:
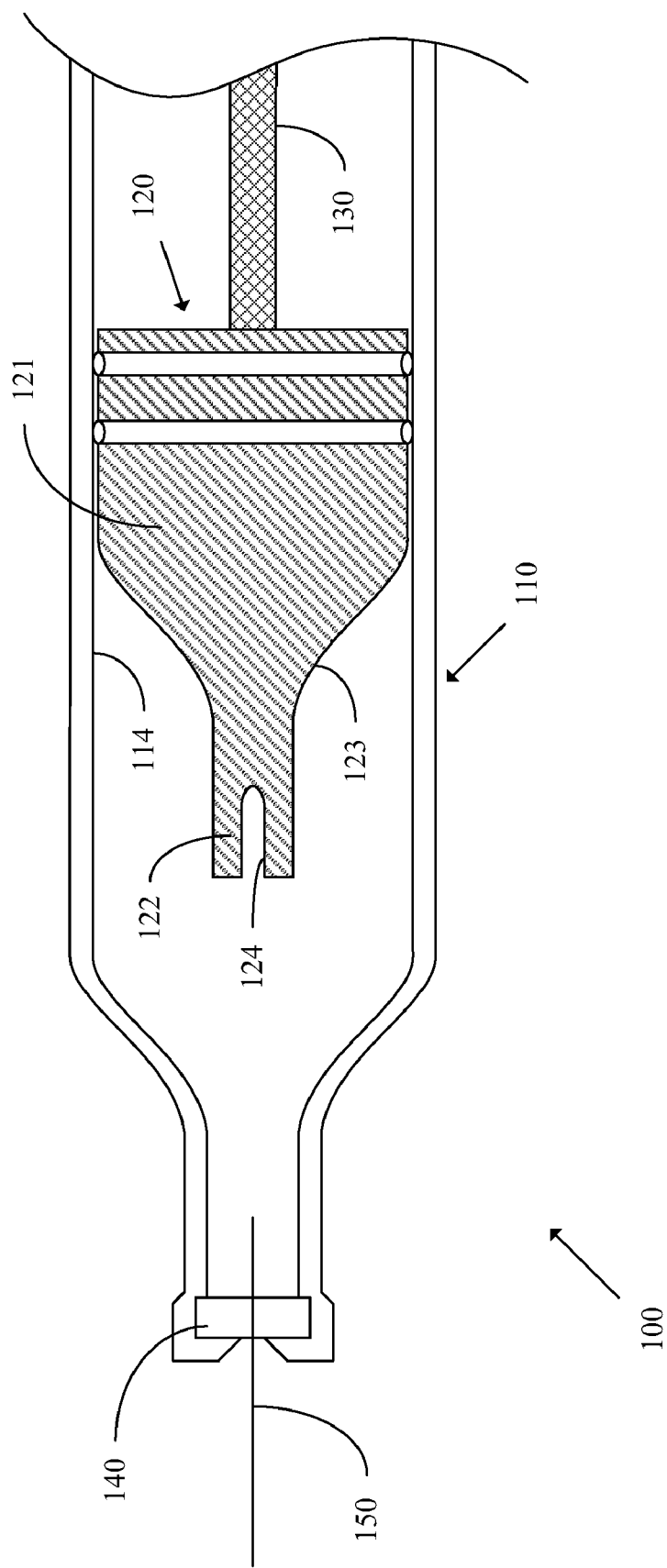
FIG. 7B illustrates a cross-sectional view of a system in accordance with an embodiment of the present invention.

In various embodiments, the method then continues to S14. In S14, the plunger head 120 is retracted within the reservoir 110 to allow a fluidic medium to flow through the needle 150 and into the reservoir 110. For example, the plunger arm 130 may be retracted by a motor (not shown in FIG. 7A) or by a pulling force exerted by a user to cause the plunger head 120 to retract within the reservoir 110. FIG. 7B illustrates a cross-sectional view of the system 100 in accordance with an embodiment of the present invention when the plunger head 120 has been partially retracted within the reservoir 110. By retracting the plunger head 120 within the reservoir 110, the fluidic medium is able to pass through the needle 150 and into the hollow interior of the reservoir 110. For example, one end of the needle 150 may be in the reservoir 110, and another end of the needle 150 may be in a vial (not shown in FIG. 7B) or other container that stores the fluidic medium, and the fluidic medium may pass from the vial to the reservoir 110 through the needle 150. In some embodiments, the needle 150 is part of a transfer guard or other similar device. Because an amount of air in the reservoir 110 was limited prior to filling the reservoir 110, an amount of air bubbles in the fluidic medium is also limited when the fluidic medium is filled into the reservoir 110. Limiting or reducing a presence of air bubbles in the fluidic medium is beneficial, because it limits an amount of air bubbles that are later expelled from the reservoir 110 into a patient or user, and thus helps to improve a delivery accuracy when delivering a specified amount of the fluidic medium to a user.

With reference to FIGS. 7A, 7B, and 8, the method of FIG. 8 may then continue to S15 in which the needle 150 is removed from the reservoir 110. In various embodiments, the septum 140 is a self-healing septum, and when the needle 150 is removed from the reservoir 110 and the septum 140, the septum 140 closes such that the fluidic medium is contained within the reservoir 110. The method may then continue to S16. In S16, the septum 140 of the reservoir 110 is pierced with another needle. For example, the septum 140 of the reservoir 110 may be pierced with a needle of a connector of an infusion path, such as a needle of the connector 56 (refer to FIG. 2) of the infusion path 50 (refer to FIG. 2). The method then continues to S17.

In S17, the plunger head 120 is advanced within the reservoir 110 until at least a portion of the another needle is received within the cavity of the plunger head 120, so as to expel the fluidic medium from the reservoir 110 through the another needle. FIG. 7A illustrates the system 100 when the plunger head 120 has been substantially fully advanced within the reservoir 110. When the plunger head 120 is advanced within the reservoir 110, the close fitting contour of the plunger head 120 to the interior surface of the reservoir 110 limits or reduces a volume of wasted fluidic medium that remains in the reservoir 110. Thus, by having a plunger head 120 with a plunger neck portion 122 that is shaped to very closely fit within the neck portion 112 of the reservoir 110 when the plunger head 120 is fully advanced, a presence of air bubbles in a fluidic medium may be limited during filling of the reservoir 110, and a volume of wasted fluidic medium may be reduced when the fluidic medium is expelled from the reservoir 110. The method then ends in S18.

Figure 7C:
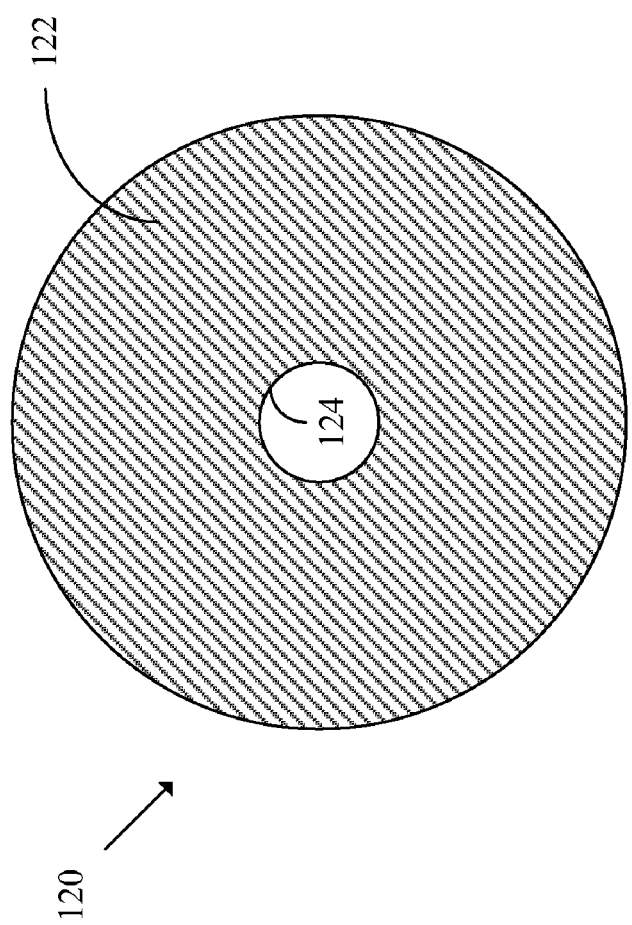
FIG. 7C illustrates a cross-sectional view from a front direction of a plunger neck portion of a plunger head in accordance with an embodiment of the present invention.
Figure 7D:
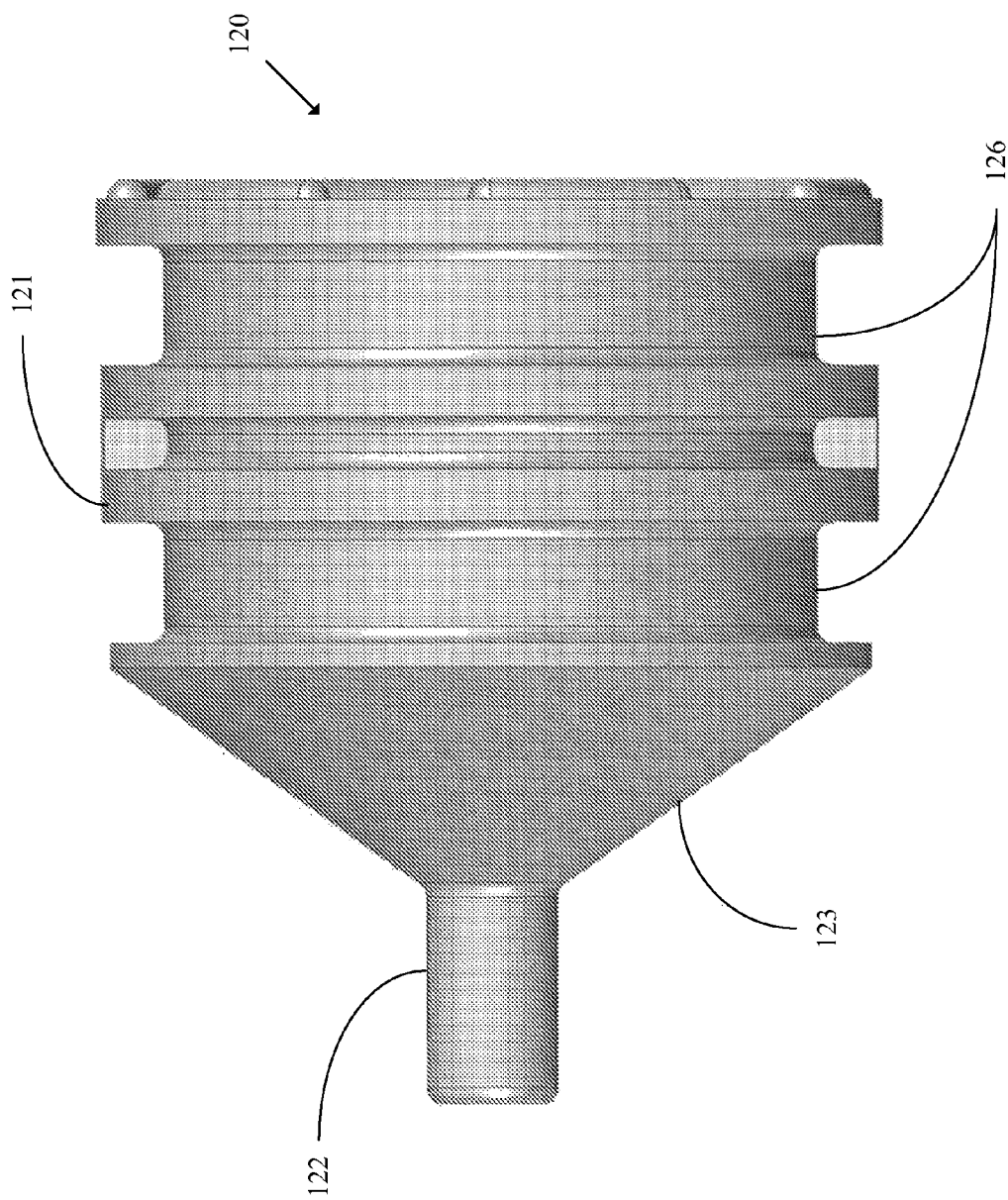
FIG. 7D illustrates a side view of a plunger head in accordance with an embodiment of the present invention.

FIG. 7C illustrates a cross-sectional view from a front direction of the plunger neck portion 122 of the plunger head 120 in accordance with an embodiment of the present invention. The plunger neck portion 122 includes the cavity 124 for accommodating a needle. In various embodiments, the cavity 124 is positioned substantially near a center of a face of the plunger neck portion 122. FIG. 7D illustrates a side view of the plunger head 120 in accordance with an embodiment of the present invention. The plunger head 120 includes the plunger body portion 121, the plunger neck portion 122, and the plunger sloped portion 123. In various embodiments, the plunger body portion 121 includes one or more depressions or cavities 126 in which the one or more seals 125 (refer to FIG. 7A) may be placed.

FIGS. 9A, 10A, 11A, 12A, 12C, 14A, and 14B illustrate systems in accordance with various embodiments of the present invention that include reservoirs with geometries that allow for capturing air bubbles so as to reduce a number of air bubbles that are delivered with a fluidic medium. Such systems allow for air bubble management since they have bubble trapping shapes and, by reducing a number of air bubbles that are delivered with a fluidic medium, such systems may be able to improve a delivery accuracy when attempting to deliver a specified volume of the fluidic medium. Thus, such systems provide reservoir geometries that allow for capturing a greater amount of air bubbles than with standard reservoir geometries, so that the captured air bubbles remain in the reservoir and are not dispensed with the fluidic medium.

In some embodiments, the systems in FIGS. 9A, 10A, 11A, 12A, 12C, 13A, 14A, and 14B may include similar elements as elements of embodiments of the delivery device 12 (refer to FIGS. 2 and 3), in which case the reservoirs in those systems would correspond to the reservoir 40 (refer to FIGS. 2, 3, and 6C). In various embodiments, reservoirs of the systems in FIGS. 9A, 10A, 11A, 12A, 12C, 13A, 14A, and 14B may be made of a material, such as but not limited to a suitable metal, plastic, ceramic, glass, composite material, or the like. In various embodiments, the plunger heads of the systems in those figures may be made of a suitably rigid material such as, but not limited to, metal, plastic, ceramic, glass, composite material, or the like. In various other embodiments, the plunger heads in those systems may be made of a compressible material such as, but not limited to, an elastically compressible plastic, rubber, silicone, or the like.

Figure 9A:
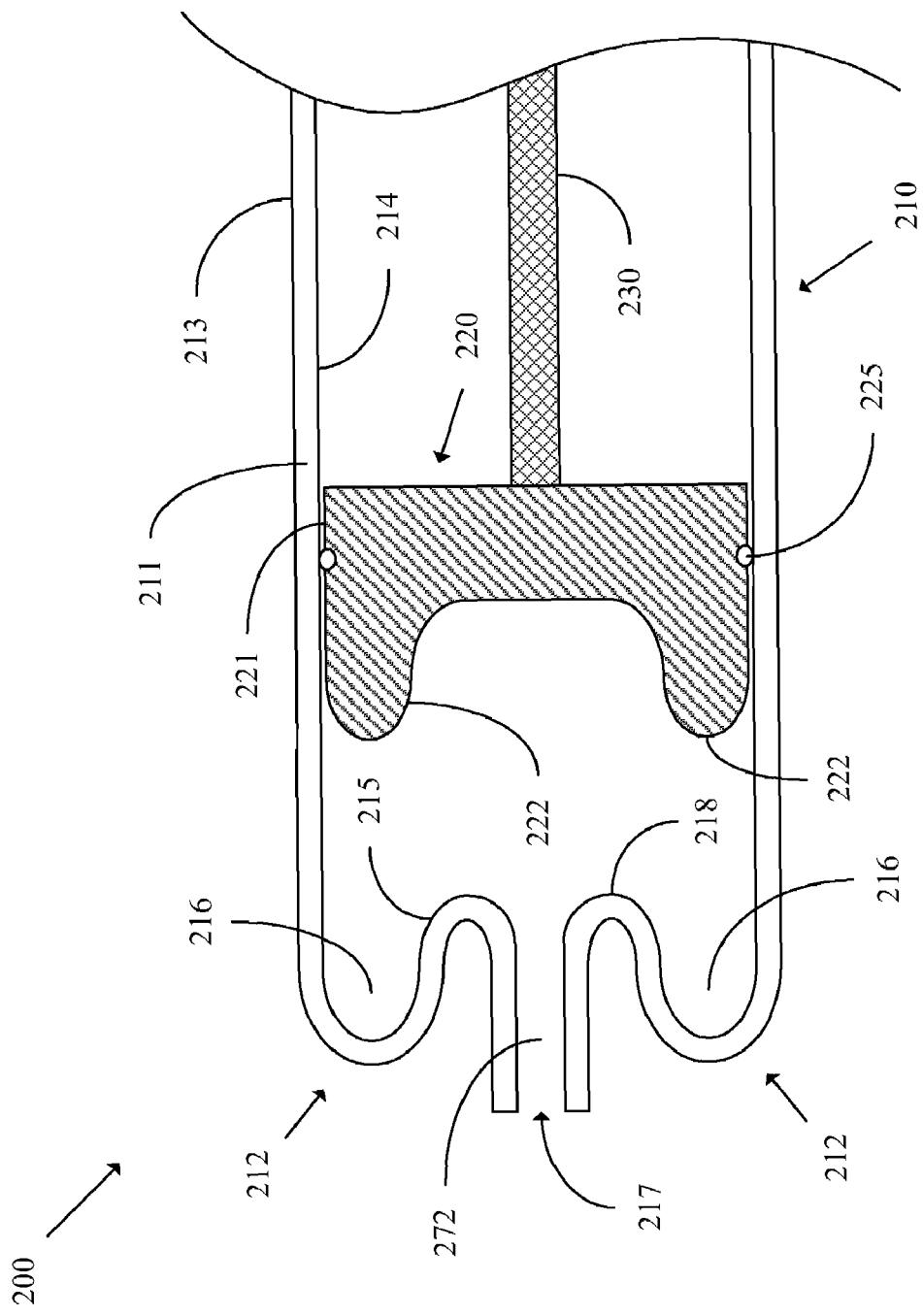
FIG. 9A illustrates a cross-sectional view of a system in accordance with an embodiment of the present invention.

FIG. 9A illustrates a cross-sectional view of a system 200 in accordance with an embodiment of the present invention. The system 200 includes a reservoir 210, a plunger head 220, and a plunger arm 230. The reservoir 210 includes a reservoir body portion 211, a bubble trap portion 212, and a port 217. The reservoir 210 has an outer surface 213 and an inner surface 214. The inner surface 214 of the reservoir 210 defines a hollow interior of the reservoir 210, and the hollow interior of the reservoir 210 is able to contain a fluidic medium. The port 217 of the reservoir 210 allows for the fluidic medium to be filled into or expelled from the hollow interior of the reservoir 210. The reservoir body portion 211 of the reservoir 210 may have any suitable shape, such as but not limited to, a cylinder shape, a tube shape, a barrel shape, a spherical shape, a shape with a rectangular cross-section, or the like.

The plunger head 220 is located within the reservoir 210, and is moveable in an axial direction of the reservoir 210, to expand or contract a volume of the reservoir 210 in which a fluidic medium may be contained. The plunger head 220 is connected to the plunger arm 230, such that movement of the plunger arm 230 in the axial direction of the reservoir 210 causes movement of the plunger head 220 in the axial direction of the reservoir 210. The plunger head 220 includes a plunger body portion 221 and a plunger protruding portion 222. In various embodiments, the plunger head 220 further includes one or more seals 225 that surround a portion of the plunger body portion 221. In various embodiments, the one or more seals 225 may be made of any suitable material, such as but not limited to, rubber, plastic, composite material, or the like.

The bubble trap portion 212 of the reservoir 210 is shaped to have a volume 216 within an interior of the reservoir 210, such that air bubbles in a fluidic medium may be trapped in the volume 216 when the fluidic medium is expelled from the reservoir 210 through the port 217. In various embodiments, an interior surface of the bubble trap portion 212 is curved or angled near the port 217, so as to define the volume 216. In some embodiments, the bubble trap portion 212 extends from the reservoir body portion 211 of the reservoir 210 past a point 218 of the reservoir 210 where a fluidic medium from an interior volume of the reservoir body portion 211 is able to move into an area or channel 272 of the reservoir 210 that leads to the port 217.

In various embodiments, the reservoir 210 is shaped such that as the plunger head 220 is advanced within the reservoir 210, a fluidic medium is able to pass through the port 217 while air bubbles in the reservoir 210 collect in the volume 216 defined by a curved or angled surface of the bubble trap portion 212 of the reservoir 210. Such a geometry of the reservoir 210 allows for decreasing an amount of air bubbles that are delivered with a fluidic medium as compared with traditional reservoir geometries. In some embodiments, the bubble trap portion 212 of the reservoir 210 is curved outward from an interior volume defined by the reservoir body portion 211, and a fluidic medium is able to pass directly from the interior volume defined by the reservoir body portion 211 to the port 217. In some embodiments, a surface 215 of the bubble trap portion 212 of the reservoir 210 includes a surface finish or material such that air bubbles substantially do not stick to the surface 215 and are shunted away from the port 217 toward the volume 216. In various embodiments, such a surface finish or material includes a hydrophobic material, a hydrophilic material, or other suitable material.

The plunger body portion 221 is shaped such that a contour of the plunger body portion 221 substantially matches or is substantially the same as an inner contour of the reservoir body portion 211 of the reservoir 210. In various embodiments, the plunger body portion 221 has a diameter that is slightly smaller than a diameter of the inner surface of the reservoir body portion 211 of the reservoir 210, such that the plunger head 220 is able to slide within the reservoir 210. In some embodiments, a seal 225 on the plunger body portion 221 is in contact with the inner surface of the reservoir body portion 211 of the reservoir 210 when the plunger head 220 is within the reservoir 210.

In various embodiments, the plunger protruding portion 222 is shaped such that a contour of the plunger protruding portion 222 substantially matches or is substantially the same as an inner contour of the bubble trap portion 212 of the reservoir 210. In some embodiments, the plunger protruding portion 222 is curved and protrudes from the plunger body portion 221. In various embodiments, the plunger protruding portion 222 has a size that is slightly smaller than a region defined by the inner surface of the bubble trap portion 212 of the reservoir 210, such that the plunger protruding portion 222 is able to slide within the volume 216 of the reservoir 210, and such that a space for a dead volume of air is left when the plunger head 220 is fully advanced within the reservoir 210. Thus, in various embodiments, the geometry of the reservoir 210 and the plunger head 220 allow for capturing air bubbles in a volume 216 of the bubble trap portion 212 when a fluidic medium is being expelled from the port 217 of the reservoir 210.

In various embodiments, the plunger protruding portion 222 has a size such that when the plunger head 220 is fully advanced within the reservoir 210, the plunger protruding portion 222 substantially fills the volume 216 of the bubble trap portion 212. Also, in various embodiments, the plunger protruding portion 222 fills less than all of the volume 216 of the bubble trap portion 212 when the plunger head 220 is fully advanced within the reservoir 210, so that one or more air pockets for holding air exist between the plunger protruding portion 222 and an inner surface of the bubble trap portion 212 when the plunger head 220 is fully advanced within the reservoir 210. In some embodiments, the plunger protruding portion 222 extends at least partially into the volume 216 of the bubble trap portion 212 when the plunger head 220 is sufficiently advanced within the reservoir 210.

Figure 9B:
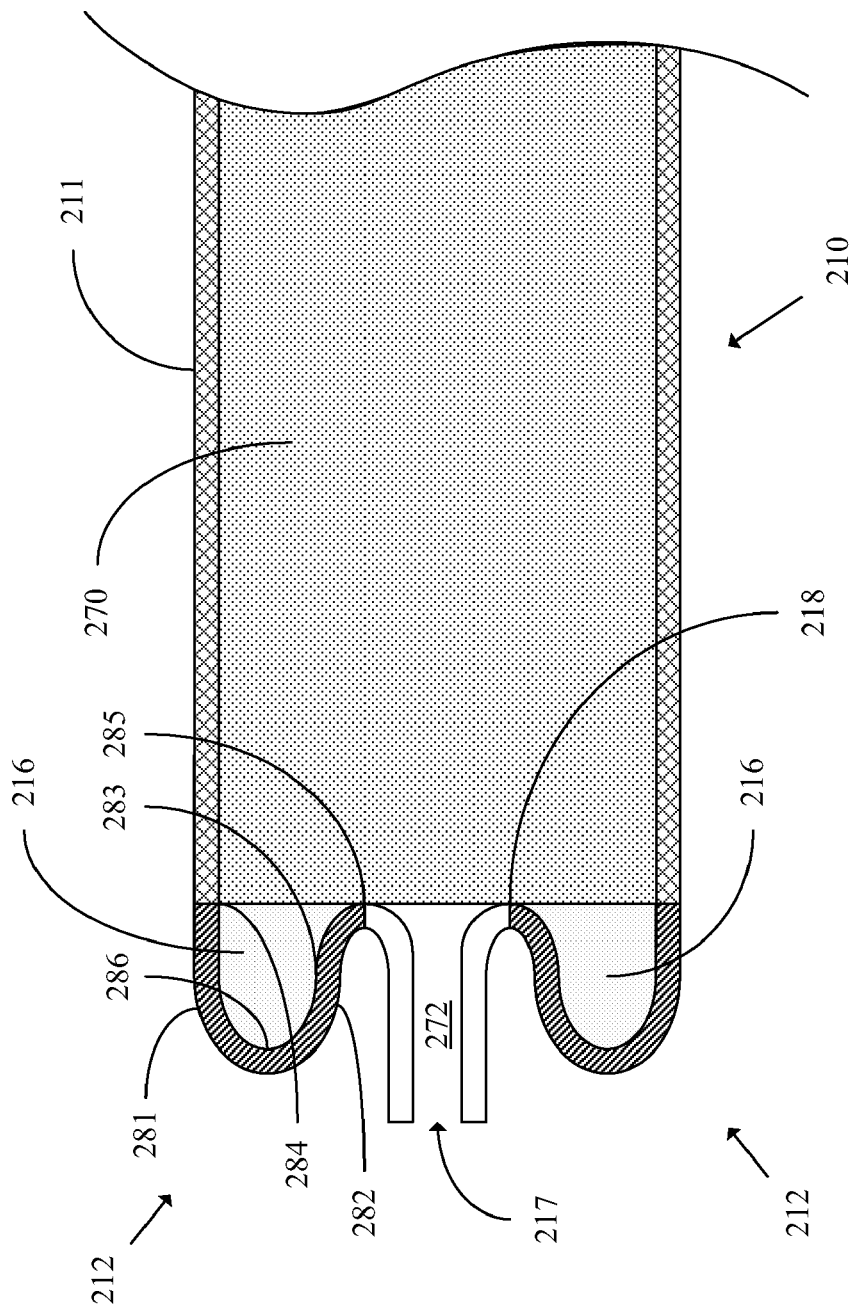
FIG. 9B illustrates a cross-sectional view of a reservoir in accordance with an embodiment of the present invention.

FIG. 9B illustrates a cross-sectional view of the reservoir 210 in accordance with an embodiment of the present invention. FIG. 9B is shaded to highlight various features of the reservoir 210. The reservoir 210 includes the reservoir body portion 211, the bubble trap portion 212, and the port 217. The reservoir body portion 211 has an interior volume 270 for containing a fluidic medium. The port 217 is in fluid flow communication with the interior volume 270 of the reservoir body portion 211. The bubble trap portion 212 has the volume 216 in fluid flow communication with the interior volume 270 of the reservoir body portion 211 for trapping air bubbles that are in the fluidic medium as the fluidic medium is being expelled from the interior volume 270.

In various embodiments, the port 217 is located to a particular side of the interior volume 270, and the bubble trap portion 212 is located to the particular side of the interior volume 270. Also, in various embodiments, the bubble trap portion 212 has a first portion 281 that extends from the reservoir body portion 211 away from the interior volume 270, and a second portion 282 that returns back toward the interior volume 270. In some embodiments, the reservoir body portion 211 and the bubble trap portion 212 are formed together as a single seamless unit. Also, in some embodiments, the first portion 281 of the bubble trap portion 212 extends from the reservoir body portion 211 away from the interior volume 270 and the second portion 282 of the bubble trap portion 212 extends from the first portion 281 toward the interior volume 270.

In various embodiments, the bubble trap portion 212 includes a curved surface 283 having a first end region 284, a second end region 285, and a middle region 286 between the first end region 284 and the second end region 285. In some embodiments, the first end region 284 and the second end region 285 are closer to the interior volume 270 of the reservoir body portion 211 than the middle region 286 is to the interior volume 270. Also, in some embodiments, the first end region 284 is in contact with the reservoir body portion 211, and the second end region 285 is located adjacent to the interior volume 270 of the reservoir body portion 211.

In various embodiments, the curved surface 283 of the bubble trap portion 212 is in contact with the fluidic medium when the fluidic medium is in the volume 216 of the bubble trap portion 212. In further embodiments, the curved surface 283 is approximately U-shaped. FIG. 9B illustrates a cross-sectional view, but in three-dimensions the bubble trap portion 212 may be shaped, for example, approximately as a semi-toroid. In various embodiments, the reservoir 210 is shaped such that in order for a fluidic medium to flow from the volume 216 of the bubble trap portion 212 to the port 217, the fluidic medium must flow through the interior volume 270 of the reservoir body portion 211. In some embodiments, the reservoir 210 includes the channel 272 that leads from the interior volume 270 of the reservoir body portion 211 to the port 217, and the bubble trap portion 212 encircles at least a portion of the channel 272.

Figure 10A:
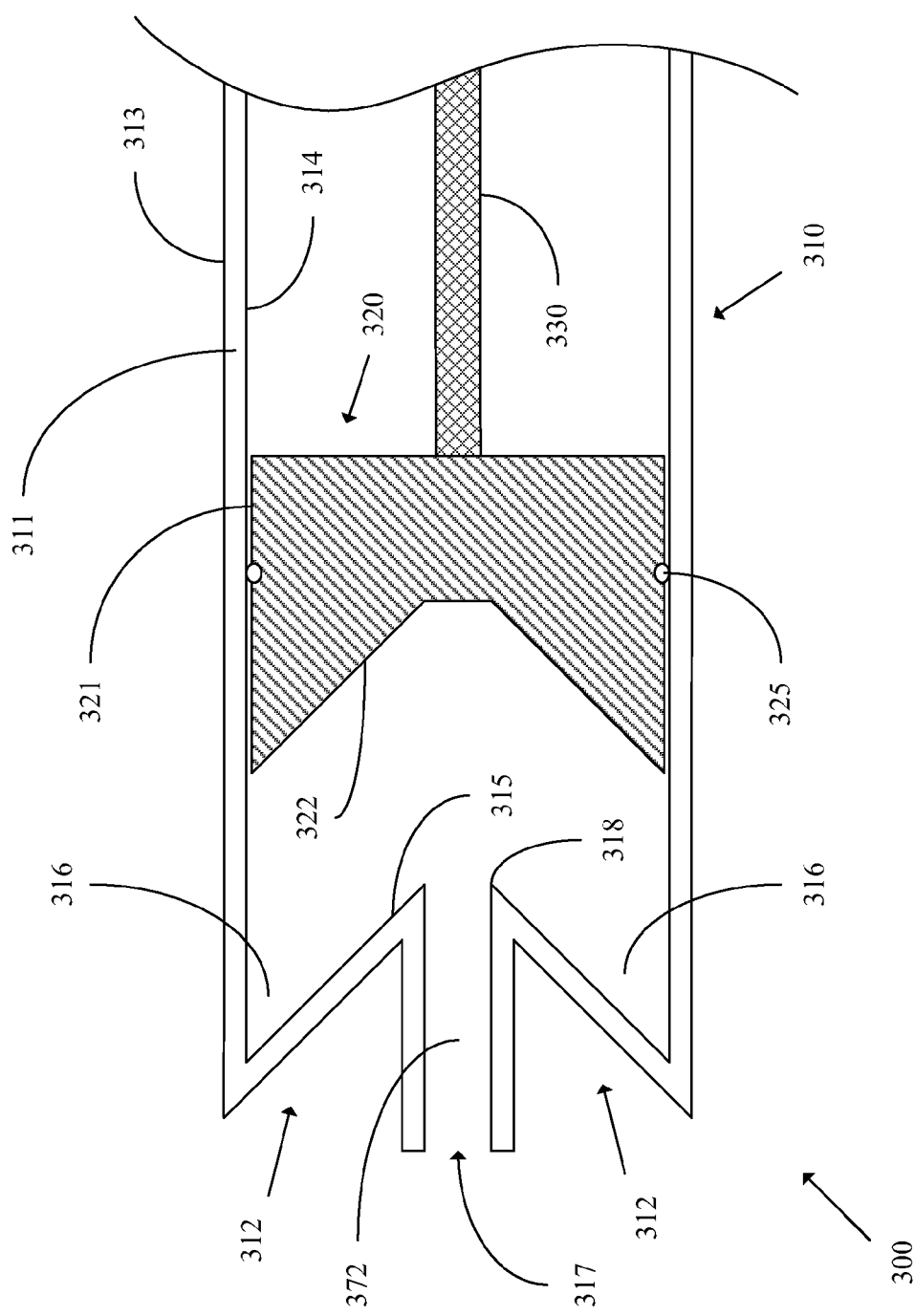
FIG. 10A illustrates a cross-sectional view of a system in accordance with an embodiment of the present invention.

FIG. 10A illustrates a cross-sectional view of a system 300 in accordance with an embodiment of the present invention. The system 300 includes a reservoir 310, a plunger head 320, and a plunger arm 330. The reservoir 310 includes a reservoir body portion 311, a bubble trap portion 312, and a port 317. The reservoir 310 has an outer surface 313 and an inner surface 314. The inner surface 314 of the reservoir 310 defines a hollow interior of the reservoir 310, and the hollow interior of the reservoir 310 is able to contain a fluidic medium. The port 317 of the reservoir 310 allows for the fluidic medium to be filled into or expelled from the hollow interior of the reservoir 310. The reservoir body portion 311 of the reservoir 310 may have any suitable shape, such as but not limited to, a cylinder shape, a tube shape, a barrel shape, a spherical shape, a shape with a rectangular cross-section, or the like.

The plunger head 320 is located within the reservoir 310, and is moveable in an axial direction of the reservoir 310, to expand or contract a volume of the reservoir 310 in which a fluidic medium may be contained. The plunger head 320 is connected to the plunger arm 330, such that movement of the plunger arm 330 in the axial direction of the reservoir 310 causes movement of the plunger head 320 in the axial direction of the reservoir 310. The plunger head 320 includes a plunger body portion 321 and a plunger protruding portion 322. In various embodiments, the plunger head 320 further includes one or more seals 325 that surround a portion of the plunger body portion 321.

The bubble trap portion 312 of the reservoir 310 is shaped so as to form a volume 316 within an interior of the reservoir 310, such that air bubbles in a fluidic medium may be trapped in the volume 316 of the bubble trap portion 312 when the fluidic medium is expelled from the reservoir 310 through the port 317. In various embodiments, an interior surface of the bubble trap portion 312 is angled at a substantially straight angle near the port 317, so as to define the volume 316. In some embodiments, the bubble trap portion 312 extends from the reservoir body portion 311 of the reservoir 310 past a point 318 of the reservoir 310 where a fluidic medium from an interior volume of the reservoir body portion 311 is able to move into an area or channel 372 of the reservoir 310 that leads to the port 317.

In various embodiments, the reservoir 310 is shaped such that as the plunger head 320 is advanced within the reservoir 310, a fluidic medium is able to pass through the port 317 while air bubbles in the reservoir 310 collect in the volume 316 defined by a substantially straight angled surface of the bubble trap portion 312 of the reservoir 310. Such a geometry of the reservoir 310 may allow for decreasing an amount of air bubbles that are delivered with a fluidic medium as compared with traditional reservoir geometries. In some embodiments, the bubble trap portion 312 of the reservoir 310 is angled outward from an interior region of the reservoir 310 defined by the reservoir body portion 311, and a fluidic medium is able to pass directly from the interior region of the reservoir 310 defined by the reservoir body portion 311 to the port 317. In some embodiments, a surface 315 of the bubble trap portion 312 of the reservoir 310 includes a surface finish or material such that air bubbles substantially do no stick to the surface 315 and are shunted away from the port 317 toward the volume 316.

The plunger body portion 321 is shaped such that a contour of the plunger body portion 321 substantially matches or is substantially the same as a contour of an inner surface of the reservoir body portion 311 of the reservoir 310. In various embodiments, the plunger body portion 321 has a diameter that is slightly smaller than a diameter of the inner surface of the reservoir body portion 311 of the reservoir 310, such that the plunger head 320 is able to slide within the reservoir 310. In some embodiments, the one or more seals 325 on the plunger body portion 321 are in contact with the inner surface of the reservoir body portion 311 of the reservoir 310 when the plunger head 320 is within the reservoir 310.

In various embodiments, the plunger protruding portion 322 is shaped such that a contour of the plunger protruding portion 322 substantially matches or is substantially the same as an inner contour of the bubble trap portion 312 of the reservoir 310. In some embodiments, the plunger protruding portion 322 is angled from the plunger body portion 321 at a substantially straight angle and protrudes from the plunger body portion 321. In various embodiments, the plunger protruding portion 322 has a size that is slightly smaller than a region defined by the inner surface of the bubble trap portion 312 of the reservoir 310, such that the plunger protruding portion 322 is able to slide within the volume 316 of the bubble trap portion 312, and such that a space for a dead volume of air is left when the plunger head 320 is fully advanced within the reservoir 310. Thus, in various embodiments, the geometry of the reservoir 310 and the plunger head 320 allow for capturing air bubbles in a volume 316 of the bubble trap portion 312 when a fluidic medium is being expelled from the port 317 of the reservoir 310.

In various embodiments, the plunger protruding portion 322 has a size such that when the plunger head 320 is fully advanced within the reservoir 310, the plunger protruding portion 322 substantially fills the volume 316 of the bubble trap portion 312. Also, in various embodiments, the plunger protruding portion 322 fills less than all of the volume 316 of the bubble trap portion 312 when the plunger head 320 is fully advanced within the reservoir 310, so that one or more air pockets for holding air exist between the plunger protruding portion 322 and an inner surface of the bubble trap portion 312 when the plunger head 320 is fully advanced within the reservoir 310. In some embodiments, the plunger protruding portion 322 extends at least partially into the volume 316 of the bubble trap portion 312 when the plunger head 320 is sufficiently advanced within the reservoir 310.

Figure 10B:
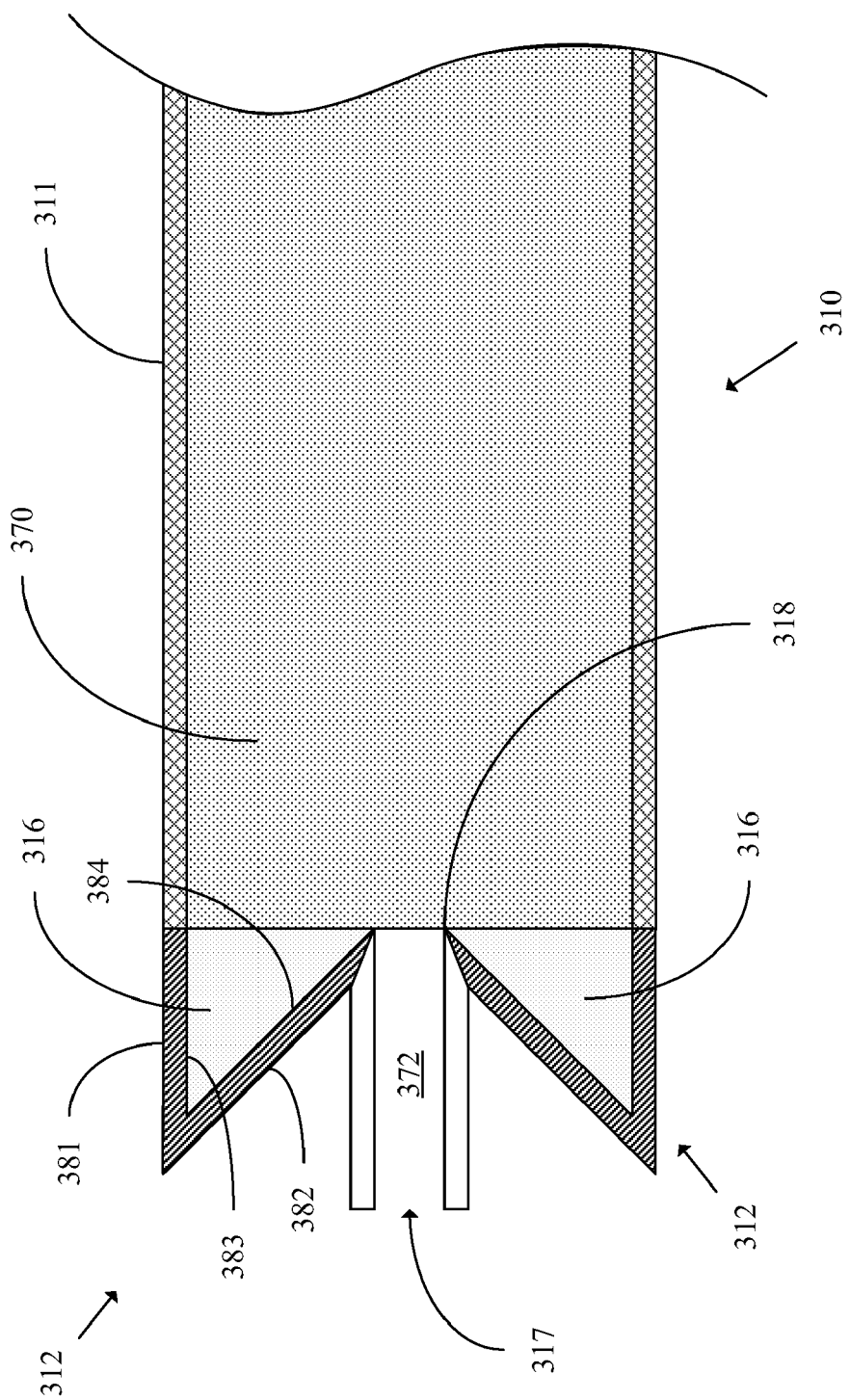
FIG. 10B illustrates a cross-sectional view of a reservoir in accordance with an embodiment of the present invention.

FIG. 10B illustrates a cross-sectional view of the reservoir 310 in accordance with an embodiment of the present invention. FIG. 10B is shaded to highlight various features of the reservoir 310. The reservoir 310 includes the reservoir body portion 311, the bubble trap portion 312, and the port 317. The reservoir body portion 311 has an interior volume 370 for containing a fluidic medium. The port 317 is in fluid flow communication with the interior volume 370 of the reservoir body portion 311. The bubble trap portion 312 has the volume 316 in fluid flow communication with the interior volume 370 of the reservoir body portion 311 for trapping air bubbles that are in the fluidic medium as the fluidic medium is being expelled from the interior volume 370.

In various embodiments, the port 317 is located to a particular side of the interior volume 370, and the bubble trap portion 312 is located to the particular side of the interior volume 370. Also, in various embodiments, the bubble trap portion 312 has a first portion 381 that extends from the reservoir body portion 311 away from the interior volume 370, and a second portion 382 that returns back toward the interior volume 370. In some embodiments, the reservoir body portion 311 and the bubble trap portion 312 are formed together as a single seamless unit. Also, in some embodiments, the first portion 381 of the bubble trap portion 312 extends from the reservoir body portion 311 away from the interior volume 370 and the second portion 382 of the bubble trap portion 312 extends from the first portion 381 toward the interior volume 370.

In various embodiments, the reservoir 310 is shaped such that in order for a fluidic medium to flow from the volume 316 of the bubble trap portion 312 to the port 317, the fluidic medium must flow through the interior volume 370 of the reservoir body portion 311. In some embodiments, the reservoir 310 includes the channel 372 that leads from the interior volume 370 of the reservoir body portion 311 to the port 317, and the bubble trap portion 312 encircles at least a portion of the channel 372.

In various embodiments, the bubble trap portion 312 includes a first surface 383 that defines an edge of the volume 316 of the bubble trap portion 312, and a second surface 384 that defines another edge of the volume 316 of the bubble trap portion 312, where the second surface 384 is positioned at an angle with respect to the first surface 383. In some embodiments, the angle between the first surface 383 and the second surface 384 is less than 90 degrees. Also, in some embodiments, the first surface 383 is planar with respect to an inner surface of the reservoir body portion 311 of the reservoir 310. In various embodiments, the port 317 is located to a particular side of the interior volume 370 and the first portion 381 of the bubble trap portion 312 extends from the reservoir body portion 311 to the particular side.

Figure 11A:
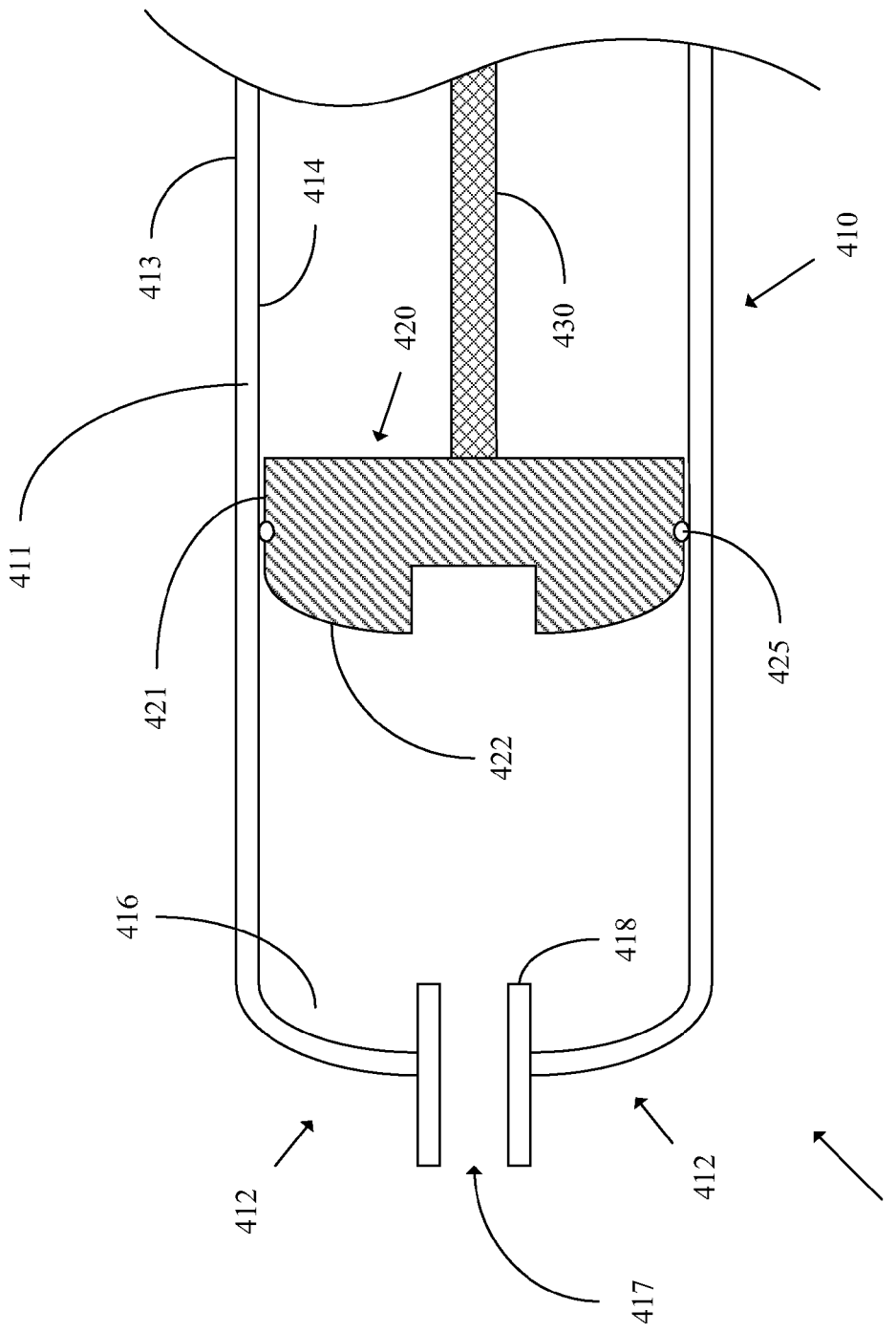
FIG. 11A illustrates a cross-sectional view of a system in accordance with an embodiment of the present invention.

FIG. 11A illustrates a cross-sectional view of a system 400 in accordance with an embodiment of the present invention. The system 400 includes a reservoir 410, a plunger head 420, and a plunger arm 430. The reservoir 410 includes a reservoir body portion 411, a bubble trap portion 412, and a port 417. The reservoir 410 has an outer surface 413 and an inner surface 414. The inner surface 414 of the reservoir 410 defines a hollow interior of the reservoir 410, and the hollow interior of the reservoir 410 is able to contain a fluidic medium. The port 417 of the reservoir 410 allows for the fluidic medium to be filled into or expelled from the hollow interior of the reservoir 410. The reservoir body portion 411 of the reservoir 410 may have any suitable shape, such as but not limited to, a cylinder shape, a tube shape, a barrel shape, a spherical shape, a shape with a rectangular cross-section, or the like.

The plunger head 420 is located within the reservoir 410, and is moveable in an axial direction of the reservoir 410, to expand or contract a volume of the reservoir 410 in which a fluidic medium may be contained. The plunger head 420 is connected to the plunger arm 430, such that movement of the plunger arm 430 in the axial direction of the reservoir 410 causes movement of the plunger head 420 in the axial direction of the reservoir 410. The plunger head 420 includes a plunger body portion 421 and a plunger protruding portion 422. In various embodiments, the plunger head 420 further includes one or more seals 425 that surround a portion of the plunger body portion 421.

The bubble trap portion 412 of the reservoir 410 is shaped so as to form a volume 416 within an interior of the reservoir 410, such that air bubbles in a fluidic medium may be trapped in the volume 416 of the bubble trap portion 412 when the fluidic medium is expelled from the reservoir 410 through the port 417. In various embodiments, the reservoir 410 is shaped such that as the plunger head 420 is advanced within the reservoir 410, a fluidic medium is able to pass through the port 417 while air bubbles in the reservoir 410 collect in the volume 416 of the reservoir 410. Such a geometry of the reservoir 410 may allow for decreasing an amount of air bubbles that are delivered with a fluidic medium as compared with traditional reservoir geometries.

The plunger body portion 421 is shaped such that a contour of an outer surface of the plunger body portion 421 substantially matches or is substantially the same as a contour of an inner surface of the reservoir body portion 411 of the reservoir 410. In various embodiments, the plunger body portion 421 has a diameter that is slightly smaller than a diameter of the inner surface of the reservoir body portion 411 of the reservoir 410, such that the plunger head 420 is able to slide within the reservoir 410. In some embodiments, the one or more seals 425 on the plunger body portion 421 are in contact with the inner surface of the reservoir body portion 411 of the reservoir 410 when the plunger head 420 is within the reservoir 410. In various embodiments, the plunger protruding portion 422 is shaped such that a contour of an outer surface of the plunger protruding portion 422 substantially matches or is substantially the same as a contour of an inner surface of the bubble trap portion 412 of the reservoir 410.

Figure 11B:
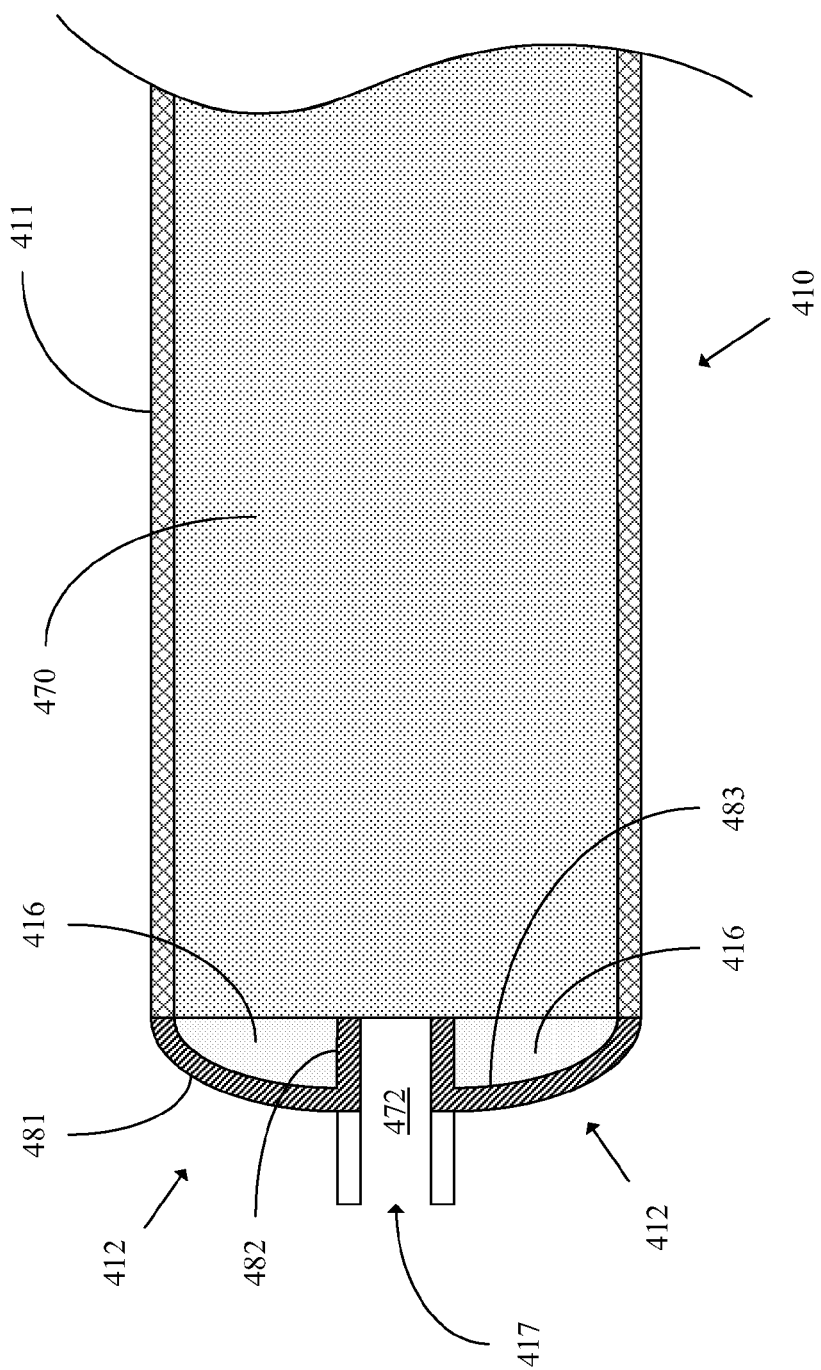
FIG. 11B illustrates a cross-sectional view of a reservoir in accordance with an embodiment of the present invention.

FIG. 11B illustrates a cross-sectional view of the reservoir 410 in accordance with an embodiment of the present invention. FIG. 11B is shaded to highlight various features of the reservoir 410. The reservoir 410 includes the reservoir body portion 411, the bubble trap portion 412, and the port 417. The reservoir body portion 411 has an interior volume 470 for containing a fluidic medium. The port 417 is in fluid flow communication with the interior volume 470 of the reservoir body portion 411. The bubble trap portion 412 has the volume 416 in fluid flow communication with the interior volume 470 of the reservoir body portion 411 for trapping air bubbles that are in the fluidic medium as the fluidic medium is being expelled from the interior volume 470.

In various embodiments, the port 417 is located to a particular side of the interior volume 470, and the bubble trap portion 412 is located to the particular side of the interior volume 470. Also, in various embodiments, the bubble trap portion 412 has a first portion 481 that extends from the reservoir body portion 411 away from the interior volume 470, and a second portion 482 that returns back toward the interior volume 470. In some embodiments, the reservoir body portion 411 and the bubble trap portion 412 are formed together as a single seamless unit. Also, in some embodiments, the first portion 481 of the bubble trap portion 412 extends from the reservoir body portion 411 away from the interior volume 470 and the second portion 482 of the bubble trap portion 412 extends from the first portion 481 toward the interior volume 470.

In various embodiments, the bubble trap portion 412 includes a curved surface 483. In some embodiments, the curved surface 483 of the bubble trap portion 412 is in contact with the fluidic medium when the fluidic medium is in the volume 416 of the bubble trap portion 412. In various embodiments, the reservoir 410 is shaped such that in order for a fluidic medium to flow from the volume 416 of the bubble trap portion 412 to the port 417, the fluidic medium must flow through the interior volume 470 of the reservoir body portion 411. In some embodiments, the reservoir 410 includes a channel 472 that leads from the interior volume 470 of the reservoir body portion 411 to the port 417, and the bubble trap portion 412 encircles at least a portion of the channel 472.

With reference to FIGS. 11A and 11B, in various embodiments, the plunger protruding portion 422 is shaped such that a contour of the plunger protruding portion 422 substantially matches or is substantially the same as an inner contour of the bubble trap portion 412 of the reservoir 410. In some embodiments, the plunger protruding portion 422 is at least partially curved and protrudes from the plunger body portion 421. Also, in some embodiments, the plunger protruding porting includes a surface that is substantially parallel to an inner surface of the reservoir body portion 411 of the reservoir 410. In various embodiments, the plunger protruding portion 422 has a size that is slightly smaller than a region defined by the inner surface of the bubble trap portion 412 of the reservoir 410, such that the plunger protruding portion 422 is able to slide within the volume 416 of the reservoir 410, and such that a space for a dead volume of air is left when the plunger head 420 is fully advanced within the reservoir 410. Thus, in various embodiments, the geometry of the reservoir 410 and the plunger head 420 allow for capturing air bubbles in a volume 416 of the bubble trap portion 412 when a fluidic medium is being expelled from the port 417 of the reservoir 410.

In various embodiments, the plunger protruding portion 422 has a size such that when the plunger head 420 is fully advanced within the reservoir 410, the plunger protruding portion 422 substantially fills the volume 416 of the bubble trap portion 412. Also, in various embodiments, the plunger protruding portion 422 fills less than all of the volume 416 of the bubble trap portion 412 when the plunger head 420 is fully advanced within the reservoir 410, so that one or more air pockets for holding air exist between the plunger protruding portion 422 and an inner surface of the bubble trap portion 412 when the plunger head 420 is fully advanced within the reservoir 410. In some embodiments, the plunger protruding portion 422 extends at least partially into the volume 416 of the bubble trap portion 412 when the plunger head 420 is sufficiently advanced within the reservoir 410.

FIG. 12A illustrates a cross-sectional view of a system 500 in accordance with an embodiment of the present invention. The system 500 includes a reservoir 510, a plunger head 520, and a plunger arm 530. In various embodiments, the system 500 further includes a needle 550. The reservoir 510 is similar to the reservoir 210 of the system 200 (refer to FIG. 9A), and includes a reservoir body portion 511 and a bubble trap portion 512. The bubble trap portion 512 defines a volume 516 for trapping air bubbles. Thus, the reservoir 510 has an air trap geometry that allows for capturing air bubbles.

The plunger head 520 is similar to the plunger head 220 of the system 200 (refer to FIG. 9A). The plunger head 520 includes a plunger body portion 521 and a plunger protruding portion 522. The plunger head 520 further includes a depression or relief 523 for allowing at least a portion of the needle 550 to be inserted into an interior of the reservoir 510 when the plunger head 520 is fully advanced within the reservoir 510. In various embodiments, the plunger head 520 has the relief 523 for receiving at least a portion of the needle 550 when the plunger head 520 is sufficiently advanced within the reservoir 510 and the portion of the needle 550 is inserted into the reservoir 510. In various embodiments, the reservoir 510 is shaped to trap air bubbles. Also, in various embodiments, the reservoir 510 and the plunger head 520 are shaped so as to minimize a delivery of air bubbles when a fluidic medium is expelled from the reservoir 510.

FIG. 12B illustrates a cross-sectional view of the reservoir 510 in accordance with an embodiment of the present invention. FIG. 12B is shaded to highlight various features of the reservoir 510. The reservoir 510 includes the reservoir body portion 511, the bubble trap portion 512, and a port 517. The reservoir body portion 511 has an interior volume 570 for containing a fluidic medium. The port 517 is in fluid flow communication with the interior volume 570 of the reservoir body portion 511. The bubble trap portion 512 has the volume 516 in fluid flow communication with the interior volume 570 of the reservoir body portion 511 for trapping air bubbles that are in the fluidic medium as the fluidic medium is being expelled from the interior volume 570.

In various embodiments, the port 517 is located to a particular side of the interior volume 570, and the bubble trap portion 512 is located to the particular side of the interior volume 570. Also, in various embodiments, the bubble trap portion 512 has a first portion 581 that extends from the reservoir body portion 511 away from the interior volume 570, and a second portion 582 that returns back toward the interior volume 570. In some embodiments, the reservoir body portion 511 and the bubble trap portion 512 are formed together as a single seamless unit. Also, in some embodiments, the first portion 581 of the bubble trap portion 512 extends from the reservoir body portion 511 away from the interior volume 570 and the second portion 582 of the bubble trap portion 512 extends from the first portion 581 toward the interior volume 570.

In various embodiments, the bubble trap portion 512 includes a curved surface 583 having a first end region 584, a second end region 585, and a middle region 586 between the first end region 584 and the second end region 585. In some embodiments, the first end region 584 and the second end region 585 are closer to the interior volume 570 of the reservoir body portion 511 than the middle region 586 is to the interior volume 570. Also, in some embodiments, the first end region 584 is in contact with the reservoir body portion 511, and the second end region 585 is located adjacent to the interior volume 570 of the reservoir body portion 511.

In various embodiments, the curved surface 583 of the bubble trap portion 512 is in contact with the fluidic medium when the fluidic medium is in the volume 516 of the bubble trap portion 512. In further embodiments, the curved surface 583 is approximately U-shaped. FIG. 9B illustrates a cross-sectional view, but in three-dimensions the bubble trap portion 512 may be shaped, for example, approximately as a semi-toroid. In various embodiments, the reservoir 510 is shaped such that in order for a fluidic medium to flow from the volume 516 of the bubble trap portion 512 to the port 517, the fluidic medium must flow through the interior volume 570 of the reservoir body portion 511. In some embodiments, the reservoir 510 includes a channel 572 that leads from the interior volume 570 of the reservoir body portion 511 to the port 517, and the bubble trap portion 512 encircles at least a portion of the channel 572.

Figure 12C:
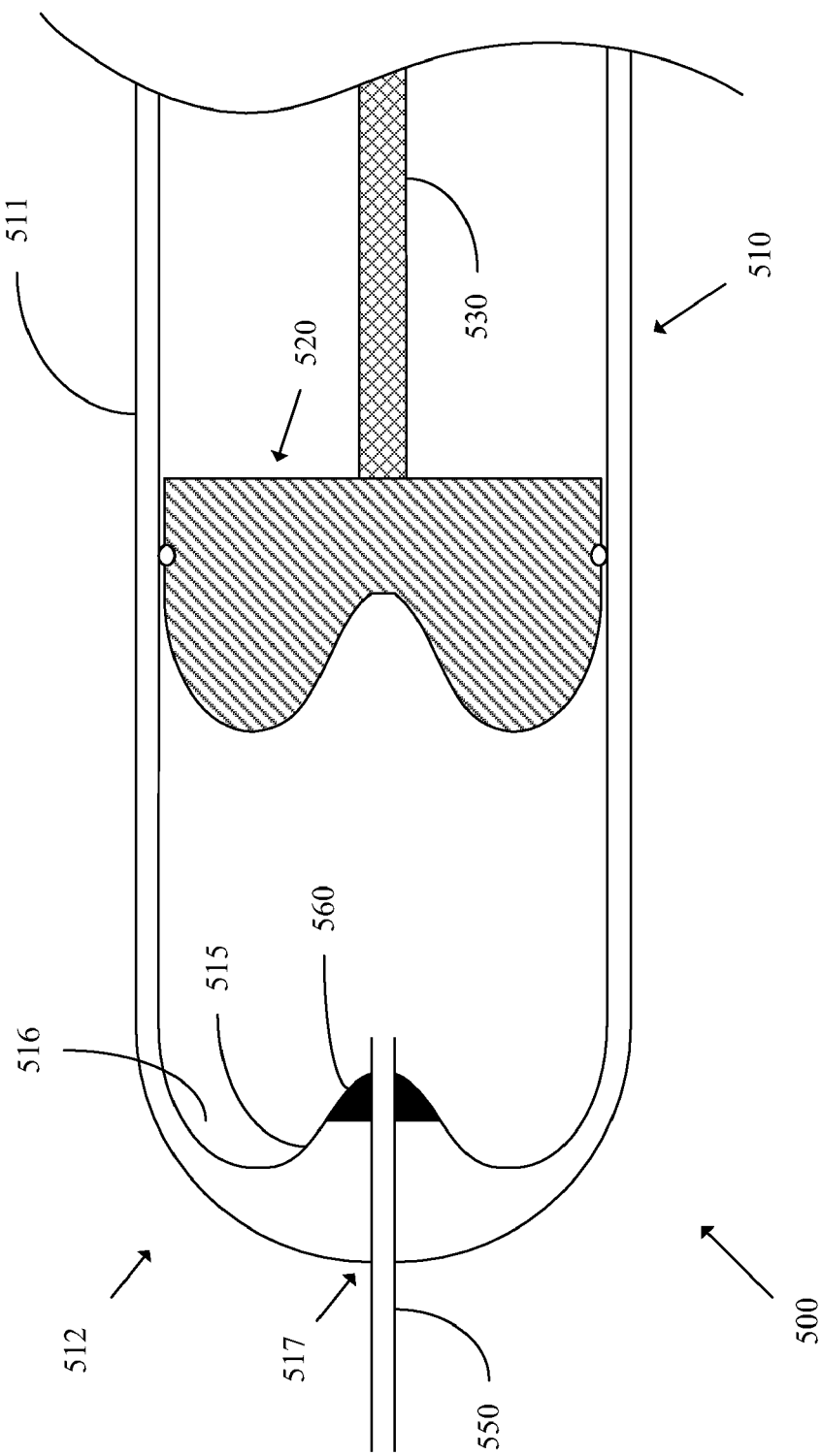
FIG. 12C illustrates a cross-sectional view of a system in accordance with an embodiment of the present invention.

FIG. 12C illustrates a cross-sectional view of the system 500 of FIG. 12A in accordance with another embodiment of the present invention. In the embodiment illustrated in FIG. 12C, the system 500 further includes a feature 560. In various embodiments, the feature 560 is located between an interior surface 515 of the bubble trap portion 512 of the reservoir 510 and a location of the reservoir 510 where a fluidic medium is able to be expelled from the reservoir 510. The feature 560 may comprise, for example, a hydrophilic material or a hydrophobic material, that will substantially keep air bubbles from being dispensed through the port 517 of the reservoir 510. As a consequence, a delivery accuracy may be able to be improved since a number of air bubbles expelled from the reservoir 510 is further limited by the feature 560. In various embodiments, the feature 560 shunts air bubbles in a fluidic medium away from the port 517 of the reservoir 510 and toward the volume 516 of the bubble trap portion 512 when the fluidic medium is being expelled from an interior volume of the reservoir body portion 511 of the reservoir 510.

Figure 13A:
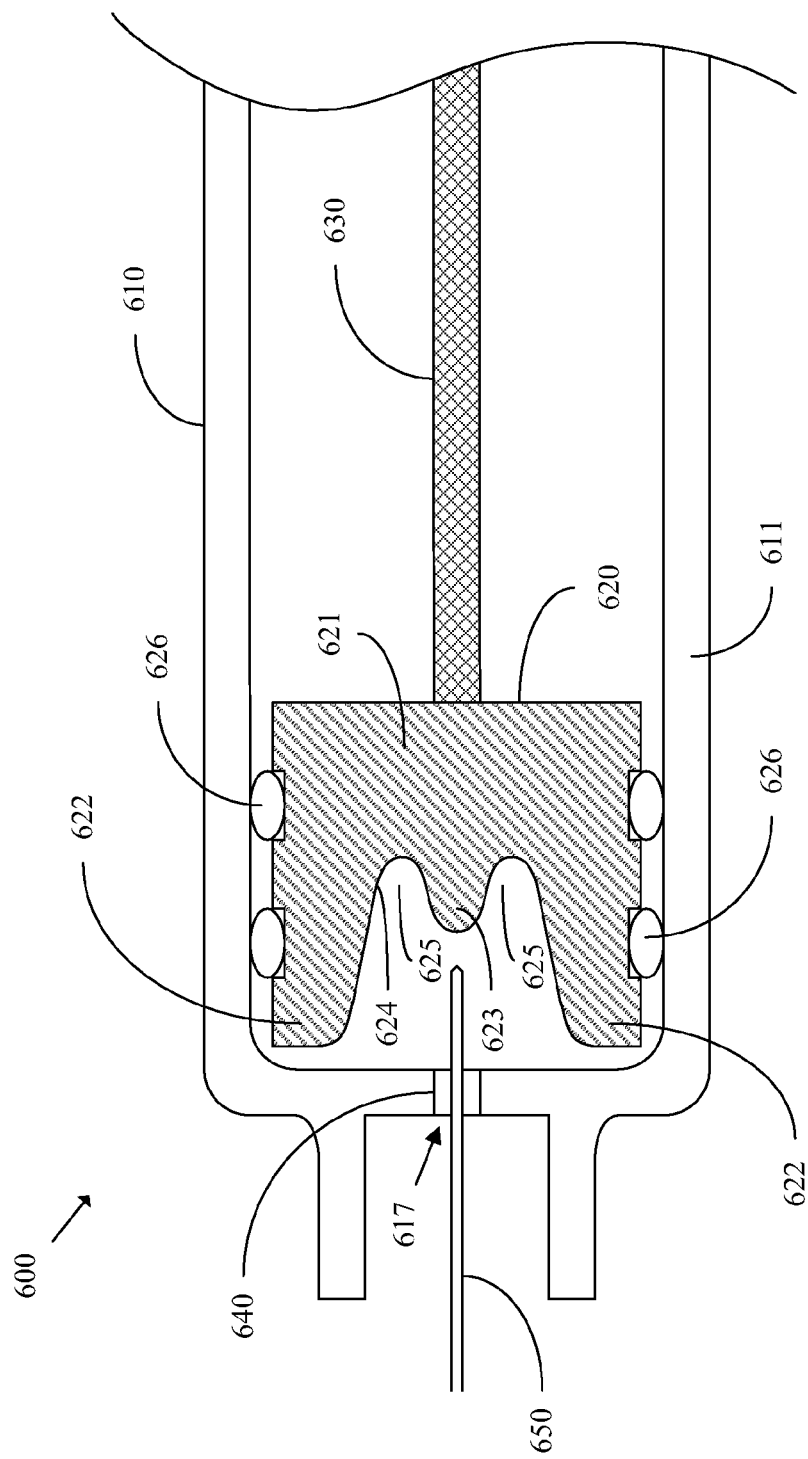
FIG. 13A illustrates a cross-sectional view of a system in accordance with an embodiment of the present invention.

FIG. 13A illustrates a cross-sectional view of a system 600 in accordance with an embodiment of the present invention. The system 600 includes a reservoir 610, a plunger head 620, and a plunger arm 630. The reservoir 610 has a hollow interior that is able to contain a fluidic medium. The reservoir 610 includes a port 617 that allows for the fluidic medium to be filled into or expelled from the hollow interior of the reservoir 610. In various embodiments, a septum 640 is located in the port 617 of the reservoir 610, where the septum 640 is able to be pierced by a needle 650. The reservoir 610 includes a reservoir body portion 611 that may have any suitable shape, such as but not limited to, a cylinder shape, a tube shape, a barrel shape, a spherical shape, a shape with a rectangular cross-section, or the like.

The plunger head 620 is located within the reservoir 610, and is moveable in an axial direction of the reservoir 610, to expand or contract a volume of the reservoir 610 in which a fluidic medium may be contained. The plunger head 620 is connected to the plunger arm 630, such that movement of the plunger arm 630 in the axial direction of the reservoir 610 causes movement of the plunger head 620 in the axial direction of the reservoir 610. The plunger head 620 is shaped to form a bubble trap region 625 for trapping air bubbles that are in the fluidic medium as the fluidic medium is expelled from the reservoir 610 by the plunger head 620. In various embodiments, the plunger head 620 includes a concave portion 624 that defines the bubble trap region 625. In various embodiments, the plunger head 620 further includes one or more seals 626 that surround a portion of the plunger head 620. In various embodiments, the one or more seals 626 may be made of any suitable material, such as but not limited to, rubber, plastic, composite material, or the like.

In various embodiments, the plunger head 620 includes a body portion 621, a first protrusion portion 622 protruding from the body portion 621, and a second protrusion portion 623 protruding from the body portion 621. In various embodiments, the bubble trap region 625 is located between the first protrusion portion 622 and the second protrusion portion 623. It should be appreciated that FIG. 13A is a cross-sectional view, and that the plunger head 620 is actually a three-dimensional object as rotated around a central axis passing in an axial direction of the reservoir 610. In various embodiments, the first protrusion portion 622 surrounds at least a portion of the second protrusion portion 623.

Figure 13B:
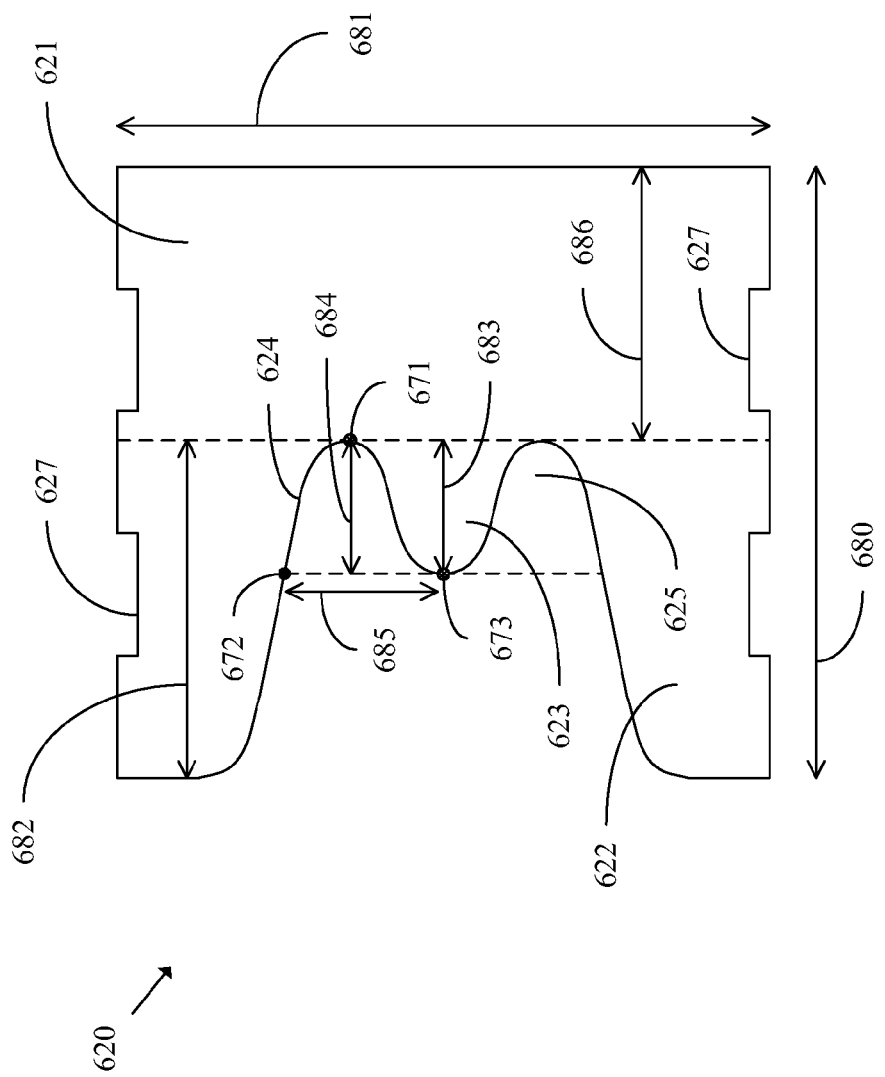
FIG. 13B illustrates a cross-sectional view of a plunger head in accordance with an embodiment of the present invention.

FIG. 13B illustrates a cross-sectional view of the plunger head 620 in accordance with an embodiment of the present invention. With reference to FIGS. 13A and 13B, in various embodiments, the first protrusion portion 622 extends a first distance 682 from the body portion 621. Also, in various embodiments, the second protrusion portion 623 extends a second distance 683 from the body portion 621. In some embodiments, the first distance 682 is greater than the second distance 683. Also, in some embodiments, the second distance 683 is greater than one-fourth of the first distance 682. In various embodiments, the second protrusion portion 623 is dome shaped.

In various embodiments, the concave portion 624 of the plunger head 620 includes a curved surface that defines the bubble trap region 625. In various embodiments, the curved surface of the concave portion 624 has a first end position 672, a second end position 673, and an innermost position 671. The first end position 672 is located on the first protrusion portion 622, and the second end position 673 is located on the second protrusion portion 623. The innermost position 671 is located at an innermost position of the concave portion 624 with respect to a depth 680 of the plunger head 620. In various embodiments, a depth 684 of the bubble trap region 625 defined by the concave portion 624 is at least greater than one-half of a width 685 of the bubble trap region 625 from the first end position 672 to the second end position 673. In various embodiments, the depth 684 of the bubble trap region 625 is greater than or equal to one-fourth of the depth 680 of the plunger head 620. In various embodiments, the body portion 621 of the plunger head 620 has a depth 686 and a width 681. In various embodiments, the plunger head 620 includes one or more seal recesses 627 in which the seals 626 are located.

A method for expelling a fluidic medium from a reservoir in accordance with an embodiment of the present invention may be performed using the system 600. In various embodiments, the plunger head 620 includes the concave portion 624 that defines the bubble trap region 625. In various embodiments, the method includes expelling the fluidic medium from the reservoir 610 using the plunger head 620, and trapping, in the bubble trap region 625 defined by the concave portion 624 of the plunger head 620, air bubbles that are in the fluidic medium as the fluidic medium is being expelled from the reservoir 610 by the plunger head 620. In various embodiments, the fluidic medium expelled from the reservoir 610 is delivered to a body of a patient through the needle 650.

Figure 14A:
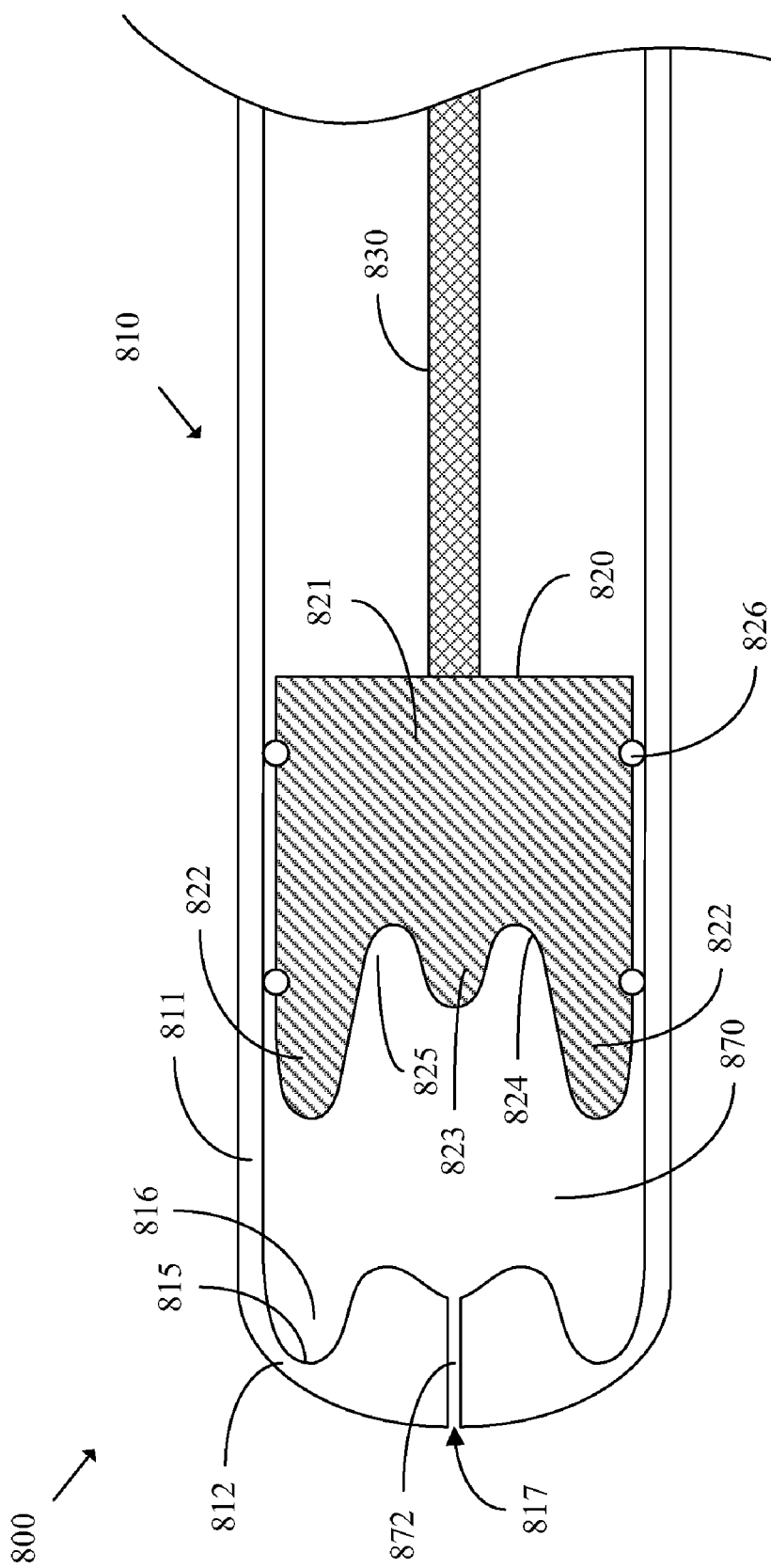
FIG. 14A illustrates a cross-sectional view of a system in accordance with an embodiment of the present invention.

FIG. 14A illustrates a cross-sectional view of a system 800 in accordance with an embodiment of the present invention. In various embodiments, the system 800 allows for delivering a fluidic medium, such as to a body of a patient. The system 800 includes a reservoir 810, a plunger head 820, and a plunger arm 830. The reservoir 810 includes a reservoir body portion 811, a reservoir bubble trap portion 812, and a port 817. The reservoir 810 has a hollow interior, and the hollow interior of the reservoir 810 is able to contain a fluidic medium. The port 817 of the reservoir 810 allows for the fluidic medium to be filled into or expelled from the hollow interior of the reservoir 810. The reservoir body portion 811 of the reservoir 810 may have any suitable shape, such as but not limited to, a cylinder shape, a tube shape, a barrel shape, a spherical shape, a shape with a rectangular cross-section, or the like.

The plunger head 820 is located within the reservoir 810, and is moveable in an axial direction of the reservoir 810, to expand or contract a volume of the reservoir 810 in which a fluidic medium may be contained. The plunger head 820 is connected to the plunger arm 830, such that movement of the plunger arm 830 in the axial direction of the reservoir 810 causes movement of the plunger head 820 in the axial direction of the reservoir 810. The plunger head 820 is shaped to form a bubble trap region 825 for trapping air bubbles that are in the fluidic medium as the fluidic medium is expelled from the reservoir 810 by the plunger head 820. In various embodiments, the plunger head 820 includes a concave portion 824 that defines the bubble trap region 825.

In various embodiments, the plunger head 820 includes a body portion 821, a first protrusion portion 822 protruding from the body portion 821, and a second protrusion portion 823 protruding from the body portion 821. In various embodiments, the bubble trap region 825 is located between the first protrusion portion 822 and the second protrusion portion 823. It should be appreciated that FIG. 14A is a cross-sectional view, and that the plunger head 820 is actually a three-dimensional object as rotated around a central axis passing in an axial direction of the reservoir 810. In various embodiments, the first protrusion portion 822 surrounds at least a portion of the second protrusion portion 823.

In various embodiments, the first protrusion portion 822 extends a first distance from the body portion 821. Also, in various embodiments, the second protrusion portion 823 extends a second distance from the body portion 821. In some embodiments, the first distance is greater than the second distance. Also, in some embodiments, the second distance is greater than one-fourth of the first distance. In various embodiments, the second protrusion portion 823 is dome shaped. In various embodiments, the concave portion 824 of the plunger head 820 includes a curved surface that defines the bubble trap region 825. In various embodiments, the curved surface of the concave portion 824 has a first end position, a second end position, and an innermost position. The first end position is located on the first protrusion portion 822, and the second end position is located on the second protrusion portion 823. The innermost position is located at an innermost position of the concave portion 824 with respect to a depth of the plunger head 820. In various embodiments, a depth of the bubble trap region 825 defined by the concave portion 824 is at least greater than one-half of a width of the bubble trap region 825 from the first end position to the second end position. In various embodiments, the depth of the bubble trap region 825 is greater than or equal to one-fourth of the depth of the plunger head 820.

The reservoir bubble trap portion 812 of the reservoir 810 is shaped to have a volume 816 within an interior of the reservoir 810, such that air bubbles in the fluidic medium may be trapped in the volume 816 when the fluidic medium is expelled from the reservoir 810 through the port 817. In various embodiments, an interior surface 815 of the reservoir bubble trap portion 812 is curved or angled near the port 817, so as to define the volume 816. In some embodiments, reservoir the bubble trap portion 812 extends from the reservoir body portion 811 of the reservoir 810 past a point of the reservoir 810 where the fluidic medium from an interior volume of the reservoir body portion 811 is able to move into an area or channel 872 of the reservoir 810 that leads to the port 817.

In various embodiments, the reservoir 810 and the plunger head 820 are shaped such that as the plunger head 820 is advanced within the reservoir 810, the fluidic medium is able to pass through the port 817 while some air bubbles in the reservoir 810 collect in the volume 816 defined by the interior surface 815 of the reservoir bubble trap portion 812 of the reservoir 810 and other air bubbles in the reservoir 810 collect in the bubble trap region 825 defined by the concave portion 824 of the plunger head 820. Such a geometry of the reservoir 810 and the plunger head 820 allows for decreasing an amount of air bubbles that are delivered with a fluidic medium as compared with traditional reservoir and plunger head geometries. In some embodiments, the reservoir bubble trap portion 812 of the reservoir 810 is curved outward from an interior volume 870 defined by the reservoir body portion 811, and a fluidic medium is able to pass directly from the interior volume 870 defined by the reservoir body portion 811 to the port 817.

In various embodiments, the body portion 821 of the plunger head 820 is shaped such that a contour of the body portion 821 substantially matches or is substantially the same as an inner contour of the reservoir body portion 811 of the reservoir 810. In various embodiments, the body portion 821 of the plunger head 820 has a diameter that is slightly smaller than a diameter of an inner surface of the reservoir body portion 811 of the reservoir 810, such that the plunger head 820 is able to slide within the reservoir 810. In some embodiments, a seal 826 on the body portion 821 of the plunger head 820 is in contact with the inner surface of the reservoir body portion 811 of the reservoir 810 when the plunger head 820 is within the reservoir 810.

In various embodiments, the reservoir body portion 811 has the interior volume 870 for containing the fluidic medium. Also, in various embodiments, the port 817 is in fluid flow communication with the interior volume 870. In various embodiments, the plunger head 820 is moveable within the reservoir 810, and the plunger head 820 is shaped to form the bubble trap region 825 for trapping air bubbles that are in the fluidic medium as the fluidic medium is being expelled from the interior volume 870 through the port 817 by the plunger head 820. Thus, in various embodiments, the geometry of the reservoir 810 and the plunger head 820 allow for capturing some air bubbles in the volume 816 of the reservoir bubble trap portion 812 and for capturing some air bubbles in the bubble trap region 825 defined by the plunger head 820 when the fluidic medium is being expelled through the port 817 of the reservoir 810.

In various embodiments, the reservoir includes the reservoir bubble trap portion 812 having the volume 816 in fluid flow communication with the interior volume 870 for trapping air bubbles that are in the fluidic medium as the fluidic medium is being expelled from the interior volume 870. In some embodiments, a contour of the first protrusion portion 822 of the plunger head 820 substantially matches an inner contour of the reservoir bubble trap portion 812. In various embodiments, the first protrusion portion 822 of the plunger head 820 is shaped and positioned such that the first protrusion portion 822 extends at least partially into the volume 816 of the reservoir bubble trap portion 812 when the plunger head 820 is sufficiently advanced within the reservoir 810. In some embodiments, the first protrusion portion 822 of the plunger head 820 is shaped and positioned such that when the plunger head 820 is fully advanced within the reservoir 810 the first protrusion portion 822 substantially fills the volume 816 of the reservoir bubble trap portion 812.

In various embodiments, the reservoir 810 is shaped such that in order for the fluidic medium to flow from the volume 816 of the reservoir bubble trap portion 812 to the port 817, the fluidic medium must flow through the interior volume 870. In some embodiments, the reservoir 810 further includes the channel 872 that leads from the interior volume 870 to the port 817. Also, in some embodiments, the reservoir bubble trap portion 812 includes a first portion that extends from the reservoir body portion 811 away from the interior volume 870, and a second portion that returns back toward the interior volume 870, where the reservoir bubble trap portion 812 encircles at least a portion of the channel 872.

With reference to FIGS. 3, 5C, 6C, and 14A, in various embodiments, the system 800 further includes the drive device 80, the disposable housing 20, and the durable housing 30, where the reservoir 810 of FIG. 14A may correspond to the reservoir 40 of FIG. 3. In some embodiments, the drive device 80 includes the drive device linkage portion 82 and the motor 84 for moving the drive device linkage portion 82. In some embodiments, the plunger arm 830 is connected to the plunger head 820, and the plunger arm 830 has a mating portion, which may include threads, teeth, or the like, for mating with the drive device linkage portion 82 of the drive device 80. In various embodiments, the disposable housing 20 allows for housing the reservoir 810 and for being secured to a user, such as the user 7 of FIG. 1. Also, in various embodiments, the durable housing 30 allows for housing the motor 84 of the drive device 80, where the durable housing 30 is configured to be selectively engaged with and disengaged from the disposable housing 20.

Figure 14B:
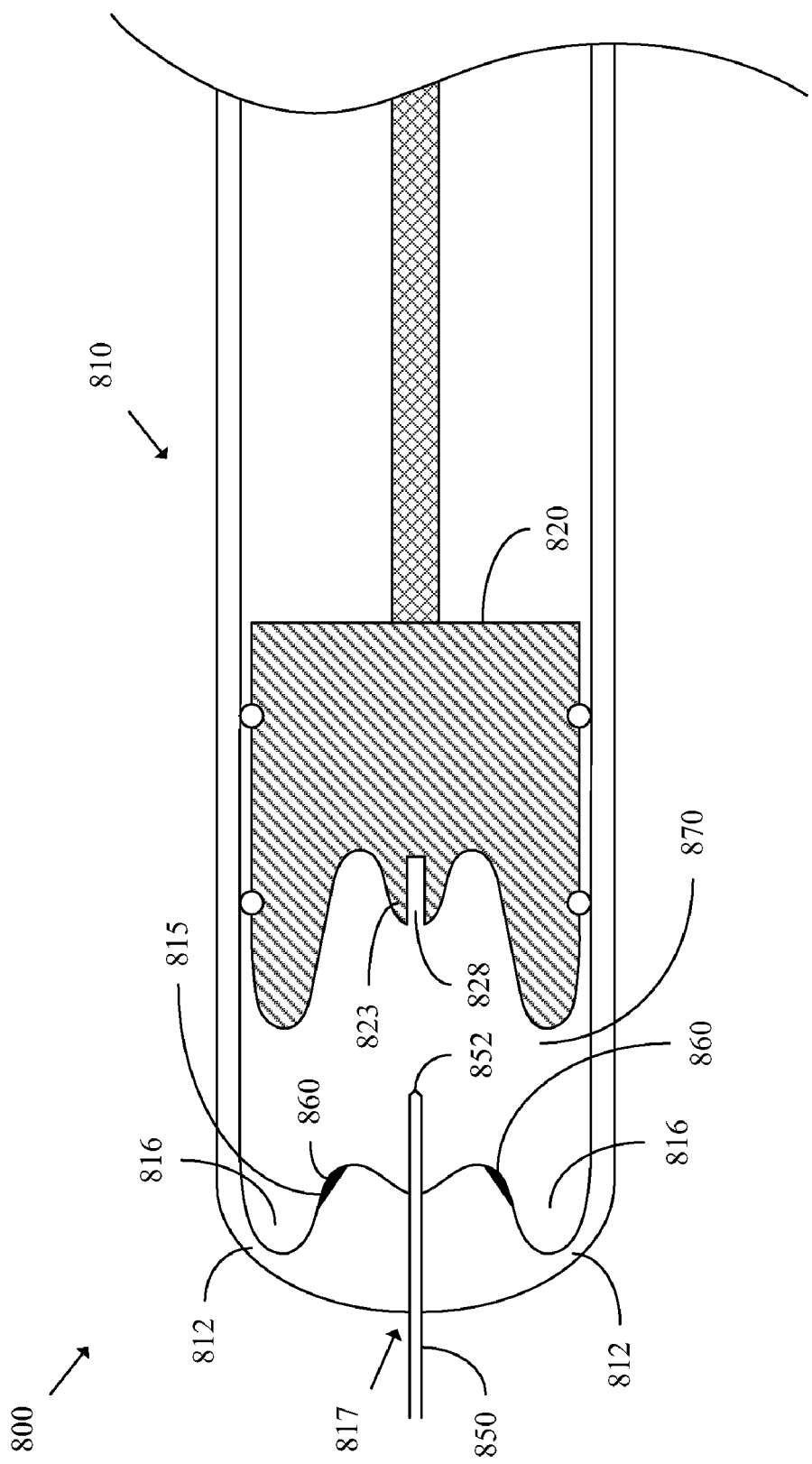
FIG. 14B illustrates a cross-sectional view of a system in accordance with an embodiment of the present invention.

FIG. 14B illustrates the system 800 in accordance with an embodiment of the present invention. In the embodiment illustrated in FIG. 14B, the second protrusion portion 823 of the plunger head 820 includes a cavity 828 for receiving a portion of a needle 850 when the plunger head 820 is sufficiently advanced within the reservoir 810. In various embodiments, the second protrusion portion 823 is aligned with the port 817, such that when the needle 850 is inserted into the port 817, an end 852 of the needle 850 is directed toward the second protrusion portion 823.

In some embodiments, the reservoir 810 includes a material 860 for shunting air bubbles in the fluidic medium away from the port 817 and toward the volume 816 of the reservoir bubble trap portion 812 when the fluidic medium is being expelled from the interior volume 870. In various embodiments, the material 860 is located on at least a portion of the interior surface 815 of the reservoir bubble trap portion 812, such that air bubbles substantially do not stick to the portion of the interior surface 815 covered with the material 860 and are shunted away from the port 817 toward the volume 816 defined by the reservoir bubble trap portion 812. In various embodiments, the material 860 includes a hydrophobic material, a hydrophilic material, or other suitable material.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. Various modifications and changes that come within the meaning and range of equivalency of the claims are intended to be within the scope of the invention.

What is claimed is:

1. A plunger head moveable within a reservoir to expel fluidic media from an interior volume of the reservoir, the plunger head comprising:

a plunger head body having a front end and a rear end opposite the front end, the front end of the plunger head body defining an end of a front portion of the interior volume, the rear end of the plunger head body defining an end of a rear portion of the interior volume, the front end of the plunger head body having a concavity for trapping air bubbles in the fluidic media as the fluidic media is expelled from the reservoir by the plunger head, the front end of the plunger head body defining a wall around the concavity; and a seal member arranged along a side surface of the plunger head body that is substantially parallel with an inner surface of the reservoir to engage the inner surface of the reservoir, the seal member arranged at a location on the side surface that is spaced apart from the front end of the plunger head body;

wherein the wall of the plunger head body is spaced apart from the inner surface of the reservoir as the fluidic media is expelled from the reservoir by the plunger head; and wherein the plunger head body and the seal member are arranged in the reservoir to prevent fluidic media from passing between the rear portion of the interior volume and the front portion of the interior volume.

2. The plunger head of claim 1, the front end of the plunger head body comprising:

a first protrusion portion protruding from the plunger head body; and a second protrusion portion protruding from the plunger head body, the concavity located between the first protrusion portion and the second protrusion portion.

3. The plunger head of claim 2, the first protrusion portion surrounding at least a portion of the second protrusion portion.

4. The plunger head of claim 3, the first protrusion portion extending a first distance from the plunger head body;

the second protrusion portion extending a second distance from the plunger head body; and the first distance greater than the second distance.

5. The plunger head of claim 4, the second distance greater than one-fourth of the first distance.

6. The plunger head of claim 2, the second protrusion portion including a cavity for receiving a portion of a needle.

7. The plunger head of claim 1, the front end of the plunger head body portion including a curved surface that defines the concavity;

the curved surface having a first end position, a second end position, and an innermost position;

wherein a depth of the concavity is at least greater than one-half of a width of the bubble trap region from the first end position to the second end position.

8. The plunger head of claim 1, the front end of the plunger head body comprising:

a protruding portion protruding from the plunger head body, the concavity located within the protruding portion.

9. The plunger head of claim 1, wherein the seal member is a separate element from the plunger head body.

10. The plunger head of claim 1, wherein the seal member arranged on the side surface of the plunger head body is located between the front end of the plunger head body and a rear end of the plunger head body portion.

11. The plunger head of claim 1, the side surface of the plunger head body having a length dimension greater than a length dimension of the seal member.

12. The plunger head of claim 1, wherein the front end of the plunger head body contacts fluidic media in a case where fluidic media is contained in the interior volume of the reservoir.

13. The plunger head of claim 1, wherein the seal member is the only portion of the plunger head that engages the inner surface of the reservoir.

14. The plunger head of claim 1, wherein the plunger head body has a uniform width dimension along its axis.

15. The plunger head of claim 1,
the front end having a protruding portion in which the concavity is disposed;
the protruding portion spaced apart from the inner surface of the reservoir.

16. The plunger head of claim 1,
the front end having a protruding portion in which the concavity is disposed;
wherein a width dimension of the protruding portion is less than a width dimension of the reservoir; and
wherein the reservoir has a uniform width dimension along the axial direction of the reservoir.

17. The plunger head of claim 1,
the front end having a protruding portion in which the concavity is disposed;
wherein a distal portion of the protruding portion is spaced apart from the inner surface of the reservoir.

18. The plunger head of claim 1, wherein the wall of the plunger head body is spaced apart from the inner surface of the reservoir when the seal member is engaged with the inner surface of the reservoir.

19. The plunger head of claim 1, wherein the concavity of the plunger head body is out of fluid communication with the rear portion of the interior volume.

20. The plunger head of claim 1, wherein the rear end of the plunger head body is free from contact of fluidic media during all movement of the plunger head body.

21. The plunger head of claim 1, wherein the plunger head body and the seal member are arranged in the reservoir to prevent fluidic media from flowing through the plunger head body.

22. The plunger head of claim 1, wherein the plunger head body and the seal member are arranged in the reservoir to prevent fluidic media from passing between the front portion of the interior volume and the rear portion of the interior volume when the plunger head body is advanced in the reservoir and when the plunger head body is withdrawn in the reservoir.

23. A system for delivering fluidic media, the system comprising:
a reservoir, the reservoir comprising:
a reservoir body portion having an interior volume for containing fluidic media, the reservoir having a port in fluid flow communication with the interior volume of the reservoir body portion;
a plunger head moveable within the reservoir to expel fluidic media contained in the interior volume of the reservoir body portion, the plunger head comprising:
a plunger head body having a front end and a rear end opposite the front end, the front end of the plunger head body defining an end of a front portion of the interior volume, the rear end of the plunger head body defining an end of a rear portion of the interior volume, the front end of the plunger head body having a concavity for trapping air bubbles in the fluidic media as the fluidic media is expelled from the interior volume of the reservoir body portion through the port of the reservoir by the plunger head, the front end of the plunger head body defining a wall around the concavity; and
a seal member arranged along a side surface of the plunger head body that is substantially parallel with an inner surface of the reservoir to engage the inner surface of the reservoir, the seal member arranged at a location on the side surface that is spaced apart from the front end of the plunger head body;
wherein the wall of the plunger head body is spaced apart from the inner surface of the reservoir as the fluidic media is expelled from the reservoir by the plunger head; and
wherein the plunger head body and the seal member are arranged in the reservoir to prevent fluidic media from passing between the rear portion of the interior volume and the front portion of the interior volume.

24. The system of claim 23, the front end of the plunger head body comprising:
a first protrusion portion protruding from the plunger head body; and
a second protrusion portion protruding from the plunger head body, the concavity located between the first protrusion portion and the second protrusion portion.

25. The system of claim 24, the first protrusion portion surrounding at least a portion of the second protrusion portion.

26. The system of claim 25,
the first protrusion portion extending a first distance from the plunger head body;
the second protrusion portion extending a second distance from the plunger head body; and
the first distance greater than the second distance.

27. The system of claim 26, the second distance greater than one-fourth of the first distance.

28. The system of claim 25, the second protrusion portion aligned with the port of the reservoir such that when a needle is inserted into the port of the reservoir, an end of the needle is directed toward the second protrusion portion.

29. The system of claim 24, the second protrusion portion including a cavity for receiving a portion of a needle.

30. The system of claim 24, the reservoir further comprising:
a reservoir bubble trap portion having a volume in fluid flow communication with the interior volume of the reservoir body portion, the reservoir bubble trap region for trapping air bubbles in the fluidic media as the fluidic media is expelled from the interior volume of the reservoir body portion.

31. The system of claim 30, the first protrusion portion shaped and positioned such that the first protrusion portion substantially fills the volume of the reservoir bubble trap portion in a case where the plunger head is fully advanced within the reservoir.

32. The system of claim 30, the reservoir shaped such that in order for the fluidic media to flow from the volume of the reservoir bubble trap portion to the port of the reservoir, the fluidic media must flow through the interior volume of the reservoir body portion.

33. The system of claim 23, the system further comprising:
a drive device including a linkage portion and a motor for moving the linkage portion;
a plunger arm connected to the plunger head, the plunger arm having a mating portion for mating with the linkage portion of the drive device;
a first housing for housing the reservoir and for being secured to a user; and
a second housing for housing the motor of the drive device, the second housing configured to be selectively engaged with and disengaged from the first housing.

34. A system for delivering fluidic media, the system comprising:
a reservoir, the reservoir comprising:
a reservoir body portion having an interior volume for containing fluidic media, the reservoir having a port in fluid flow communication with the interior volume of the reservoir body portion; and a reservoir bubble trap portion having a volume in fluid flow communication with the interior volume of the reservoir body portion, the reservoir bubble trap region for trapping air bubbles in the fluidic media as the fluidic media is expelled from the interior volume of the reservoir body portion;

a plunger head moveable within the reservoir to expel fluidic media contained in the interior volume of the reservoir body portion, the plunger head comprising:

a plunger head body having a front end, the front end of the plunger head body having a concavit for trapping air bubbles in the fluidic media as the fluidic media is expelled from the interior volume of the reservoir body portion through the port of the reservoir by the plunger head, the front end of the plunger head body defining a wall around the concavity;

the front end of the plunger head body comprising:

a first protrusion portion protruding from the plunger head body; and a second protrusion portion protruding from the plunger head body, the concavit located between the first protrusion portion and the second protrusion portion;

a seal member arranged along a side surface of the plunger head body that is substantially parallel with an inner surface of the reservoir to engage the inner surface of the reservoir, the seal member arranged at a location on the side surface that is spaced apart from the front end of the plunger head body;

wherein the wall of the plunger head body is spaced apart from the inner surface of the reservoir as the fluidic media is expelled from the reservoir by the plunger head; and wherein a contour of the first protrusion portion substantially matches an inner contour of the reservoir bubble trap portion.

35. A system for delivering fluidic media, the system comprising:

a reservoir, the reservoir comprising:

a reservoir body portion having an interior volume for containing fluidic media, the reservoir having a port in fluid flow communication with the interior volume of the reservoir body portion; and a reservoir bubble trap portion having a volume in fluid flow communication with the interior volume of the reservoir body portion, the reservoir bubble trap region for trapping air bubbles in the fluidic media as the fluidic media is expelled from the interior volume of the reservoir body portion;

a plunger head moveable within the reservoir to expel fluidic media contained in the interior volume of the reservoir body portion, the plunger head comprising:

a plunger head body having a front end, the front end of the plunger head body having a concavity for trapping air bubbles in the fluidic media as the fluidic media is expelled from the interior volume of the reservoir body portion through the port of the reservoir by the plunger head, the front end of the plunger head body defining a wall around the concavity;

the front end of the plunger head body comprising:

a first protrusion portion protruding from the plunger head body; and a second protrusion portion protruding from the plunger head body, the concavity located between the first protrusion portion and the second protrusion portion;

a seal member arranged along a side surface of the plunger head body that is substantially parallel with an inner surface of the reservoir to engage the inner surface of the reservoir, the seal member arranged at a location on the side surface that is spaced apart from the front end of the plunger head body;

wherein the wall of the plunger head body is spaced apart from the inner surface of the reservoir as the fluidic media is expelled from the reservoir by the plunger head; and the first protrusion portion shaped and positioned such that the first protrusion portion extends at least partially into the volume of the reservoir bubble trap portion when the plunger head is sufficiently advanced within the reservoir.

36. A system for delivering fluidic media, the system comprising:

a reservoir, the reservoir comprising:

a reservoir body portion having an interior volume for containing fluidic media, the reservoir having a port in fluid flow communication with the interior volume of the reservoir body portion;

a reservoir bubble trap portion having a volume in fluid flow communication with the interior volume of the reservoir body portion, the reservoir bubble trap region for trapping air bubbles in the fluidic media as the fluidic media is expelled from the interior volume of the reservoir body portion;

a material for shunting air bubbles in the fluidic media away from the port of the reservoir and toward the volume of the reservoir bubble trap portion as fluidic media is expelled from the interior volume of the reservoir body portion;

a plunger head moveable within the reservoir to expel fluidic media contained in the interior volume of the reservoir body portion, the plunger head comprising:

a plunger head bod having a front end the front end of the plunger head body having a concavity for trapping air bubbles in the fluidic media as the fluidic media is expelled from the interior volume of the reservoir body portion through the port of the reservoir by the plunger head, the front end of the plunger head body defining a wall around the concavity;

the front end of the plunger head body comprising:

a first protrusion portion protruding from the plunger head body; and a second protrusion portion protruding from the plunger head body, the concavity located between the first protrusion portion and the second protrusion portion;

a seal member arranged along a side surface of the plunger head body that is substantially parallel with an inner surface of the reservoir to engage the inner surface of the reservoir, the seal member arranged at a location on the side surface that is spaced apart from the front end of the plunger head body;

wherein the wall of the plunger head body is spaced apart from the inner surface of the reservoir as the fluidic media is expelled from the reservoir by the plunger head.

37. A system for delivering fluidic media, the system comprising;
a reservoir, the reservoir comprising:
a reservoir body portion having an interior volume for containing fluidic media, the reservoir having a port in fluid flow communication with the interior volume of the reservoir body portion;
a reservoir bubble trap portion having a volume in fluid flow communication with the interior volume of the reservoir body portion, the reservoir bubble trap region for trapping air bubbles in the fluidic media as the fluidic media is expelled from the interior volume of the reservoir body portion;
the reservoir having a channel that leads from the interior volume of the reservoir body portion to the port of the reservoir;
the reservoir bubble trap portion comprising:
a first portion that extends from the reservoir body portion away from the interior volume of the reservoir body portion; and
a second portion that returns back toward the interior volume of the reservoir body portion;
a plunger head moveable within the reservoir to expel fluidic media contained in the interior volume of the reservoir body portion, the plunger head comprising:
a plunger head body having a front end, the front end of the plunger head body having a concavity for trapping air bubbles in the fluidic media as the fluidic media is expelled from the interior volume of the reservoir body portion through the port of the reservoir by the plunger head the front end of the plunger head bod defining a wall around the concavity;
the front end of the plunger head body comprising:
a first protrusion portion protruding from the plunger head body; and
a second protrusion portion protruding from the plunger head body, the concavity located between the first protrusion portion and the second protrusion portion;
a seal member arranged along a side surface of the plunger head body that is substantially parallel with an inner surface of the reservoir to engage the inner surface of the reservoir, the seal member arranged at a location on the side surface that is spaced apart from the front end of the plunger head body;
wherein the wall of the plunger head body is spaced apart from the inner surface of the reservoir as the fluidic media is expelled from the reservoir by the plunger head; and
wherein the reservoir bubble trap portion encircles at least a portion of the channel of the reservoir.

38. A method of manufacturing a plunger head moveable within a reservoir to expel fluidic media from an interior volume of the reservoir, the method comprising:
providing a plunger head body having a front end and a rear end opposite the front end, the front end of the plunger head body defining an end of a front portion of the interior volume, the rear end of the plunger head body defining an end of a rear portion of the interior volume, the front end of the plunger head body having a concavity for trapping air in the fluidic media as the fluidic media is expelled from the reservoir by the plunger head, the front end of the plunger head body defining a wall around the concavity; and
arranging a seal member along a side surface of the plunger head body that is substantially parallel with an inner surface of the reservoir to engage the inner surface of the reservoir, the seal member arranged at a location on the side surface that is spaced apart from the front end of the plunger head body;
wherein the wall of the plunger head body is spaced apart from the inner surface of the reservoir as the fluidic media is expelled from the reservoir by the plunger head; and
wherein the plunger head body and the seal member are arranged in the reservoir to prevent fluidic media from passing between the rear portion of the interior volume and the front portion of the interior volume.

\* \* \* \* \*